(12) United States Patent
Paez-Pereda et al.

(10) Patent No.: US 9,877,947 B2
(45) Date of Patent: Jan. 30, 2018

(54) C-TERMINAL HSP90 INHIBITORS TO TREAT PITUITARY ADENOMAS

(71) Applicant: MAX-PLANCK-GESELLSCHAFT ZUR FÖRDERUNG DER WISSENSCHAFTEN E.V., Munich (DE)

(72) Inventors: Marcelo Paez-Pereda, Munich (DE); Guenter Stalla, Holzkirchen (DE)

(73) Assignee: Max-Planck-Gesellschaft zur Föderung der Wissenschaften e.V., Munich (DE)

( * ) Notice: Subject to any disclaimer, the term of this patent is extended or adjusted under 35 U.S.C. 154(b) by 33 days.

(21) Appl. No.: 14/758,888

(22) PCT Filed: Jan. 4, 2014

(86) PCT No.: PCT/EP2014/000033
§ 371 (c)(1),
(2) Date: Jul. 1, 2015

(87) PCT Pub. No.: WO2014/106623
PCT Pub. Date: Jul. 10, 2014

(65) Prior Publication Data
US 2015/0335613 A1 Nov. 26, 2015

(30) Foreign Application Priority Data
Jan. 4, 2013 (EP) .................................... 13150314

(51) Int. Cl.
| | | |
|---|---|---|
| A61K 31/357 | (2006.01) | |
| C07D 407/04 | (2006.01) | |
| A61K 36/28 | (2006.01) | |
| A61K 45/06 | (2006.01) | |
| A61K 31/573 | (2006.01) | |
| A61K 31/7048 | (2006.01) | |

(52) U.S. Cl.
CPC .......... *A61K 31/357* (2013.01); *A61K 31/573* (2013.01); *A61K 31/7048* (2013.01); *A61K 36/28* (2013.01); *A61K 45/06* (2013.01); *C07D 407/04* (2013.01)

(58) Field of Classification Search
CPC ...................................................... A61K 36/00
USPC ......................................................... 424/725
See application file for complete search history.

(56) References Cited

FOREIGN PATENT DOCUMENTS

| EP | 2388011 | 11/2011 |
|---|---|---|
| WO | WO 1996/037209 | 12/1996 |
| WO | WO 2006/050501 | 5/2006 |
| WO | WO 2007/109620 | 9/2007 |
| WO | WO 2008/0583319 | 5/2008 |
| WO | WO 2008/070472 | 6/2008 |
| WO | WO 2008/096218 | 8/2008 |
| WO | WO 2009/050136 | 4/2009 |

OTHER PUBLICATIONS

Batista, et al., "The Effects of SOM230 on Cell Proliferation and Adrenocorticotropin Secretion in Human Corticotroph Pituitary Adenomas" The Journal of Clinical Endocrinology & Metabolism (2006) 91(11):4482-4488.
Black, et al., "Bisphosphonates and Fractures of the Subtrochanteric or Diaphyseal Femur" N. Engl J. Med. (2010) 362(19):1761-1771.
Boscaro, et al., "Treatment of Pituitary-Dependent Cushing's Disease with the Multireceptor Ligand Somatostatin Analog Pasireotide (SOM230): A Multicenter, Phase II Trial" J Clin Endocrinol Metab, (2009) 94(1):115-122.
Cohen, et al., "Novel C-Terminal Hsp90 Inhibitor for Head and Neck Squamous Cell Cancer (HNSCC) with in vivo Efficacy and Improved Toxicity Profiles Compared with Standard Agents" Ann Surg Oncol (2012) 19:S483-S490.
Eskew, et al., "Development and characterization of a novel C-terminal inhibitor of Hsp90 in androgen dependent and independent prostate cancer cells" BMC Cancer (2011) 11:468.
Gažák, et al., "Silybin and Silymarin—New and Emerging Applications in Medicine" Current Medicinal Chemistry ( 2007) 14:315-338.
Heaney, et al., "Functional PPAR-y receptor is a novel therapeutic target for ACTH-secreting pituitary adenomas" Nature Medicine (2002) 8(17):1281-1287.
Heath, et al., "A Phase II Trial of 17-Allylamino-17-Demethoxygeldanamycin in Patients with Hormone-RefractoryMetastatic Prostate Cancer" Clin Cancer Res (2008)14(23):7940-7946.
Kusuma, et al., "Synthesis and biological evaluation of arylated novobiocin analogs as Hsp90 inhibitors" Bioorganic & Medicinal Chemistry Letters (2011) 21:7170-7174.
Kusuma, et al. "Synthesis and Evaluation of Novologues as C-Terminal Hsp90 Inhibitors with Cytoprotective Activity against Sensory Neuron Glucotoxicity" J. Med. Chem. (2012) 55:5797-5812.
Kvols, et al., "Pasireotide (SOM230) shows efficacy and tolerability in the treatment of patients with advanced neuroendocrine tumors refractory or resistant to octreotide LAR: results from a phase II study" Endocrine-Related Cancer (2012) 19: 657-666.
Páez-Pereda, et al., "Retinoic acid prevents experimental Cushing syndrome" The Journal of Clinical Investigation (2001) 108:1123-1131.
Petersenn, et al., "Pasireotide (SOM230) Demonstrates Efficacy and Safety in Patients with Acromegaly: A Randomized, Multicenter, Phase II Trial" Clin Endocrinol Metab, (2010) 95(6): 2781-2789.

(Continued)

*Primary Examiner* — Michael V Meller
(74) *Attorney, Agent, or Firm* — Knobbe, Martens, Olson & Bear, LLP

(57) ABSTRACT

The present invention relates to C-terminal HSP90 inhibitors, like silibinin, novobiocin and derivatives thereof, stereoisomeric forms, prodrugs, solvates, hydrates and/or pharmaceutically acceptable salts of these compounds as well as pharmaceutical compositions containing at least one of these compounds together with pharmaceutically acceptable carrier, excipient and/or diluents. Said compounds and its compositions have been identified as useful for the treatment of pituitary adenomas such as corticotroph adenomas, lactotroph adenomas, somatotroph adenomas and thyrotroph adenomas.

4 Claims, 8 Drawing Sheets

(56) References Cited

OTHER PUBLICATIONS

Rácz, et al., "An antioxidant drug, silibinin, modulates steroid secretion in human pathological adrenocortical cells" Journal of Endocrinology (1990) 124:341-345.
Trepel, et al., "Targeting the dynamic HSP90 complex in cancer" Nature Review Cancer (2010) 10:537-549.
Whitesell, et al., "Hsp90 and the chaperoning of cancer" Nature Review Cancer (2005) 5:761-772.
Yun, et al., "Novobiocin Induces a Distinct Conformation of Hsp90 and Alters Hsp90-Cochaperone-Client Interactions" Biochemistry (2004) 43:8217-8229.
Zhang, et al., "Targeting multiple signal transduction pathways through inhibition of Hsp90" J Mol Med (2004) 82:488-499.I.
Zhao, et al., "Identification and initial SAR of silybin: An Hsp90 inhibitor" Bioorganic & Medicinal Chemistry Letters (2011) 21:2659-2664.

ns, like silibinin, novobiocin and derivatives thereof, stereoisomeric forms, prodrugs, solvates, hydrates and/or pharmaceutically acceptable salts of these compounds, as well as pharmaceutical compositions containing at least one of these compounds together with pharmaceutically acceptable carrier, excipient and/or diluents. Said compounds and its compositions have been identified as useful for the treatment of pituitary adenomas such as corticotroph adenomas, lactotroph adenomas, somatotroph adenomas and thyrotroph adenomas.

C-TERMINAL HSP90 INHIBITORS TO TREAT PITUITARY ADENOMAS

The present invention relates to C-terminal HSP90 inhibitors, like silibinin, novobiocin and derivatives thereof, stereoisomeric forms, prodrugs, solvates, hydrates and/or pharmaceutically acceptable salts of these compounds, as well as pharmaceutical compositions containing at least one of these compounds together with pharmaceutically acceptable carrier, excipient and/or diluents. Said compounds and its compositions have been identified as useful for the treatment of pituitary adenomas such as corticotroph adenomas, lactotroph adenomas, somatotroph adenomas and thyrotroph adenomas.

BACKGROUND OF THE INVENTION

Pituitary tumors, also called pituitary adenomas, develop in the pituitary gland and are usually benign, but in some cases invade surrounding tissues and metastasize (Heaney A. P. and Melmed S. Nature Reviews Cancer 4:285-295, 2004). Symptoms caused by pressure from a larger pituitary tumor may include: visual field defects due to pressure on the optic nerve, increased intracranial pressure, headaches, and problems with the sense of smell. Some pituitary tumors produce increased levels of pituitary hormones, which cause different symptoms. Pituitary tumors are classified into different types according to the hormones they produce or the absence of hormone production.

Corticotroph pituitary adenomas are also called "ACTH-secreting pituitary adenomas", "Cushing's disease", or "pituitary-dependent Cushing's syndrome". Corticotroph pituitary adenomas produce high amounts of adrenocorticotropic hormone (ACTH), which leads to a stimulation of the adrenal cortisol secretion. The increased level of plama cortisol has as effect the inhibition of the ACTH release from normal pituitary cells. Finally, the high levels of ACTH and cortisol in the blood result in high blood pressure, high cholesterol, weight gain or central obesity, thinning of the skin that results in striae, muscle weakness, hyperglycemia, anxiety, insomnia, reduced libido, osteoporosis and depression. Besides humans, Cushing's disease is very frequent in dogs and horses.

Cushing's disease is not to be confused with Cushing's syndrome, which is originated in the adrenal gland or produced by therapeutic treatments with synthetic corticosteroids. In contrast to Cushing's disease, Cushing's syndrome presents normal or low (suppressed) ACTH levels. Thus, pituitary tumors and adrenal tumors represent different clinical entities, being characterized by different symptoms, being differently diagnosed and treated. Some cases of Cushing's syndrome are treated by surgical resection of both adrenal glands to eliminate endogenous glucocorticoids. The resulting lack of cortisol may cause corticotroph tumors in the pituitary gland to grow unchecked. This type of corticotroph adenoma induced by adrenalectomy secretes high amounts of ACTH and MSH and is called Nelson's syndrome.

Prolactin (PRL)-producing pituitary tumors are also called prolactinomas or lactotroph adenomas and their symptoms are galactorrhea and amenorrhea in women, impotence and gynecomastia in men.

Growth hormone (GH)-producing pituitary tumors are also called somatotroph adenomas and produce gigantism or acromegaly, severe headache, heart hypertrophy, hypertension, and diabetes mellitus. Acromegaly results in abnormal enlargement of the hands, feet, ears, nose, lips, and tongue, thickening of the skin and skull, and protrusion of the lower jaw.

Thyroid-stimulating hormone (TSH)-producing tumors secrete TSH and are also called thyrotroph adenomas. The excess of TSH hormone in the blood increases the thyroxin (T4) levels in the blood, resulting in hyperthyroidism and goiter.

Hormone-producing pituitary adenomas are functional tumors that are able to produce or secrete high amounts of hormones such as ACTH, PRL, GH and TSH. The production of such hormones is associated with a variety of side reactions in the body leading to diseases. Hormone-producing pituitary adenomas include corticotroph adenomas, lactotroph adenomas, somatotroph adenomas and thyrotroph adenomas.

In contrast to hormone-secreting pituitary adenomas, non-secreting pituitary adenomas (also called non-functioning pituitary adenomas or null cell adenomas) only produce visual field defects, hypopituitarism, nausea, vertigo, and headaches that are the result of the pressure exerted by the tumor mass on the surrounding tissues.

Pituitary adenomas are usually removed by surgery, but this approach is not always successful. In many cases, only an incomplete resection is achieved and the tumors recur. Radiation therapy is also performed in some cases, but produces side effects and the success of the treatment is low.

Some treatments like the dopamine D2 receptor agonists bromocriptine, cabergoline, or quinagolide are effective only in some cases, mainly in prolactin-secreting pituitary adenomas.

Somatostatin analogs like octreotide and pasireotide (also called Som230) are also partially effective in some cases, mainly in somatotroph and corticotroph pituitary adenomas (Batista D. L. et al., Journal of Clinical Endocrinology and Metabolism 91:4482-4488, 2006; Petersen, S. et al., Journal of Clinical Endocrinology and Metabolism 95:2781-2789, 2010; Feelders, R. A. et al., New England Journal of Medicine 362:1846-1848, 2010; Boscaro M. et al., Journal of Clinical Endocrinology and Metabolism 94:115-122, 2009). However, pasireotide frequently induces severe hyperglycemia and other side effects in patients with Cushing's disease (Kvols L. K. et al, Endocr Relat Cancer 19:657-66, 2012).

Some experimental treatments have been proposed for corticotroph pituitary adenomas such as the PPAR-gamma receptor agonist rosiglitazone (Heaney A. P. et al., Nature Medicine 8:1281-1287, 2002). Rosiglitazone, might increase the risk of cardiovascular disease and bone fractures that are of particular concern in patients with pituitary adenomas, specially corticotroph adenomas that induce osteoporosis. Retinoic acid has been studied in animals, but it has not been tested in human patients due to concerns about its possible side effects (Paez-Pereda M. et al., Journal of Clinical Investigation 108, 1123-1131, 2001). It might cause dyspnea, fever, weight gain, and peripheral edema. Glucocorticoid receptor antagonists such as mifepristone might be used to reduce the symptoms of the high glucocorticoid levels induced by corticotroph tumors (André Ulmann et al.: WO2009/050136). However, GR antagonists do not reduce corticotroph tumor proliferation or ACTH secretion and have side effects such as abdominal pain, uterine cramping, and vaginal bleeding.

In conclusion, up to present there is no effective pharmacological treatment for pituitary adenomas that are secreting or producing hormones. Such a treatment should simultaneously reduce pituitary tumor cell proliferation and hormone secretion without producing serious side effects. As a result, many patients with pituitary tumors, in particular those pituitary tumors that are secreting hormones such as corticotroph adenomas, lactotroph adenomas, somatotroph adenomas and thyrotroph adenomas, remain without an efficacious treatment.

It is the objective of the present invention to provide compounds and/or pharmaceutically acceptable salts thereof, which can be used as pharmaceutically active agents for the treatment of pituitary adenoma, wherein the pituitary adenoma is selected from corticotroph adenoma, lactotroph adenoma, somatotroph adenoma and thyrotroph adenoma, as well as compositions comprising at least one of those compounds and/or pharmaceutically acceptable salts thereof as pharmaceutically active ingredients.

The objective of the present invention is solved by the teaching of the independent claims. Further advantageous features, aspects and details of the invention are evident from the dependent claims, the description, the figures, and the examples of the present application.

BRIEF DESCRIPTION OF THE INVENTION

This invention provides new methods for treating pituitary adenomas including corticotroph adenomas, lactotroph adenomas, somatotroph adenomas and thyrotroph adenomas, with pharmaceutical compositions containing HSP90 inhibitors that bind to the C-terminal domain of HSP90, in particular silibinin, novobiocin and derivatives thereof, or extracts of milk thistle (*Silybum marianum*), such as silymarin, that contain silibinin or its derivatives.

Surprisingly, it was found that the C-terminal binding HSP90 inhibitors are able to simultaneously inhibit the proliferation of pituitary tumors and the production of hormones such as ACTH, PRL, GH and TSH in pituitary tumor cells, cells without inducing toxic side effects to healthy cells. In contrast to the conventional Hsp90 inhibitors that bind to the N-terminal domain, for example 17-AAG, only C-terminal binding inhibitors such as silibinin or novobiocin increase the activity of the glucocorticoid receptor (GR) and reduce the production of ACTH, PRL, GH and TSH in pituitary tumor cells. Therefore, HSP90 inhibitors that bind to the C-terminal domain can be used, alone or in combination with other drugs, to treat pituitary tumors, in particular corticotroph adenomas, lactotroph adenomas, somatotroph adenomas and thyrotroph adenomas, and more preferably corticotroph adenomas also called ACTH-secreting pituitary adenoma or Cushing's disease.

DESCRIPTION OF THE INVENTION

Accordingly the present invention relates to C-terminal HSP90 inhibitors for use in the treatment of pituitary adenomas, wherein the pituitary adenomas are selected from corticotroph adenomas, lactotroph adenomas, somatotroph adenomas and thyrotroph adenomas. Suitable C-terminal HSP90 inhibitors for use in the treatment of pituitary adenomas, such as corticotroph adenomas, lactotroph adenomas, somatotroph adenomas and thyrotroph adenomas are compounds of general formula (I):

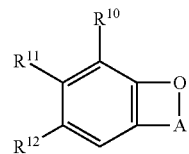

wherein
A is selected from

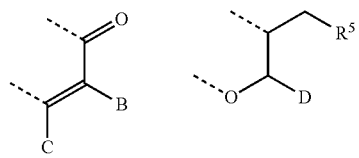

B represents —NH—C(O)—$R^{23}$, —NH—SO$_2$—$R^{23}$,

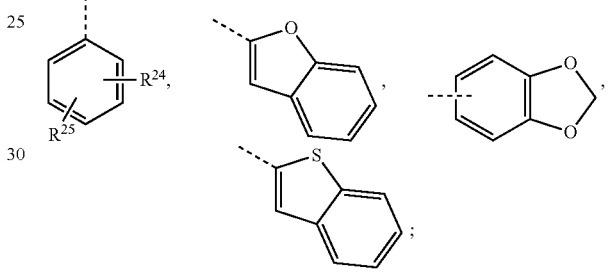

C represents —H, —OH;
D represents

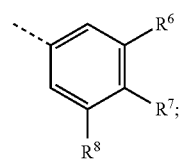

$R^{10}$ represents —H, —CH$_3$, —OCH$_3$, —F, —Cl, —Br, —I;
$R^{11}$ represents —H, —OR$^{20}$, —OCH$_2$R$^{19}$, —CO$_2$H, —CH$_2$OH, —CO$_2$CH$_3$, —NH$_2$, —NH—C(O)—CH$_3$,

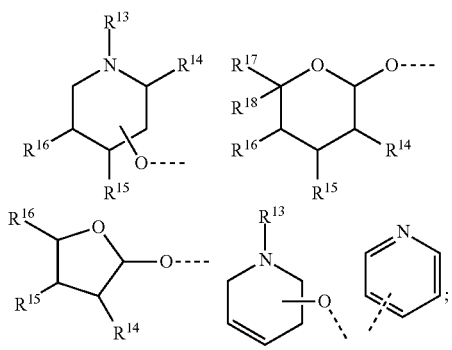

-continued

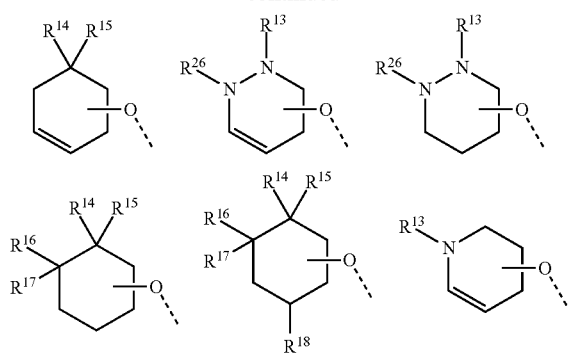

$R^{12}$ is selected from —H, —CH₃, —OCH₃,

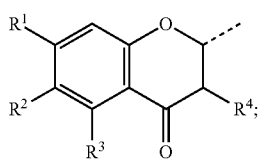

$R^{13}$ and $R^{26}$ are independently of each other —H, —CH₃, —C(O)CH₃;

$R^{14}$, $R^{15}$, $R^{16}$, $R^{17}$ and $R^{18}$ are independently of each other selected from: —H, —OH, —NH₂, —OCH₃, —OC₂H₅, —CH₃, —O—C(O)—NH₂, —O—C(O)—NHR²², —C₂H₄—S(O)₂—OCH₃, —C₂H₄—P(O)(OCH₃)₂, —CH₂—O—C(O)CH₃, —CH₂—NH—S(O)₂—OCH₃,

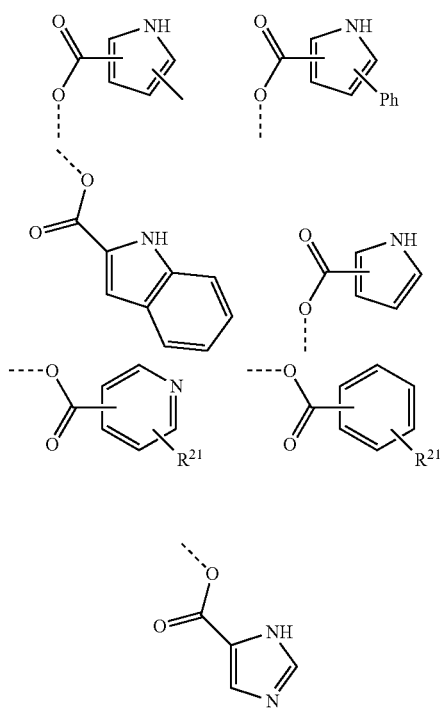

$R^{19}$ represents —CH₂—NH₂, —CH₂—NHCH₃, —CH(OH)—CH₂(OH),

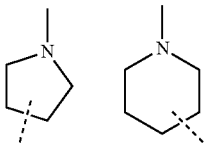

$R^{20}$ represents —H, —C(O)—CH₃, —C(O)—C₂H₅, —C(O)—C₃H₇, —C(O)—NH₂, —C(O)—NH—CH₃, —C(O)—NH—C₂H₅, —SO₂(CH₃), $R^{21}$ represents —H, —OH, —SH, —CH₃, —C₂H₅, —F, —Cl, —Br, —I;

$R^{22}$ represents —CH₃, —C₂H₅, —C₃H₇, —C₄H₉, $R^{23}$ represents —CH₃, —C₂H₅, —C₃H₇, —C₄H₉, —CH₂-Ph, —C₂H₄-Ph, —O—CH₂-Ph, -continued

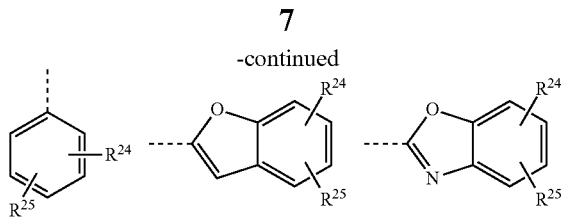

$R^{24}$ and $R^{25}$ are independently of each other selected from —H, —OH, —OCH$_3$, —OC$_2$H$_5$, —OPh, —O—CH$_2$-Ph, —CH$_2$-Ph, —C$_2$H$_4$-Ph, —NH$_2$, —NO$_2$, —CH$_2$—CH=C(CH$_3$)$_2$, —CH=CHPh, —F, —Cl, —Br, —I, —CN, —CH$_3$, —C$_2$H$_5$, —C$_3$H$_7$, —C$_4$H$_9$, —OCF$_3$, —CF$_3$, —C(CH$_3$)$_3$, -Ph, $R^{24}$ together with $R^{25}$ can form together with the 2 aromatic carbons they are connected to a cycle selected from:

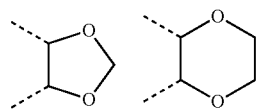

E represents —O—, —S—, —NH—, —CH$_2$—, —OCH$_2$—;

$R^1$, $R^2$, $R^3$, $R^4$, $R^6$, $R^7$ and $R^8$ represent independently of each other —H, —OH, —OCH$_3$, or —OC$_2$H$_5$; and $R^5$ represents —H, or —OR$^9$;

$R^9$ represents —H, —CH$_3$, —C$_2$H$_5$, -βGlc, -βGal, -βMal, or -βLac;

and enantiomers, stereoisomeric forms, mixtures of enantiomers, diastereomers, mixtures of diastereomers, hydrates, solvates, acid salt forms, tautomers, and racemates of the above mentioned compounds and pharmaceutically acceptable salts thereof.

Furthermore, the present invention relates to C-terminal HSP90 inhibitors of the general formula (II):

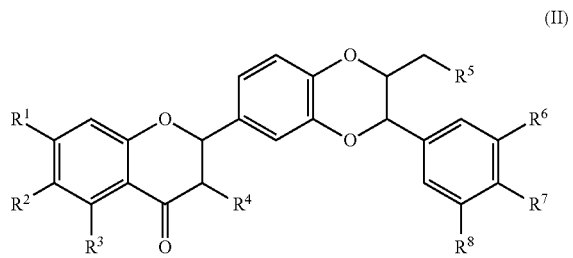

(II)

wherein
$R^1$, $R^2$, $R^3$, $R^4$, $R^6$, $R^7$ and $R^8$ represent independently of each other —H, —OH, —OCH$_3$, or —OC$_2$H$_5$;

$R^5$ represents —H, or —OR$^9$;

$R^9$ represents —H, —CH$_3$, —C$_2$H$_5$, -βGlc, -βGal, -βMal, or -βLac;

and enantiomers, stereoisomeric forms, mixtures of enantiomers, diastereomers, mixtures of diastereomers, anomers, hydrates, solvates, acid salt forms, tautomers, and racemates of the above mentioned compounds and pharmaceutically acceptable salts thereof for use in the treatment of pituitary adenoma, wherein the pituitary adenoma is selected from corticotroph adenoma, lactotroph adenoma, somatotroph adenoma and thyrotroph adenoma.

Preferred is a C-terminal HSP90 inhibitor of the following formula (III)

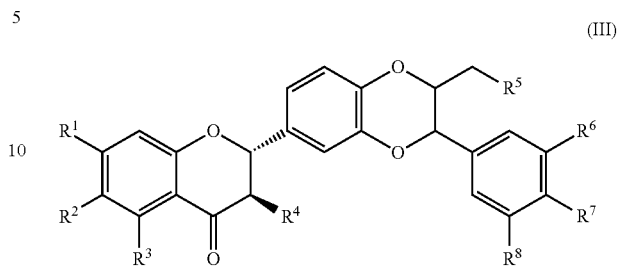

(III)

wherein
$R^1$, $R^3$, $R^4$ and $R^7$ represent —OH;

$R^2$ and $R^8$ represent —H;

$R^5$ represents —OR$^9$;

$R^6$ represents —OCH$_3$;

$R^9$ represents —H, —CH$_3$, —C$_2$H$_5$, -βGlc, -βGal, -βMal, or -βLac;

and diastereomers, mixtures of diastereomers, anomers, hydrates, solvates, acid salt forms of the above mentioned compounds and pharmaceutically acceptable salts thereof for use in the treatment of pituitary adenoma, wherein the pituitary adenoma is selected from corticotroph adenoma, lactotroph adenoma, somatotroph adenoma and thyrotroph adenoma.

The abbreviations used herein have the following meanings:

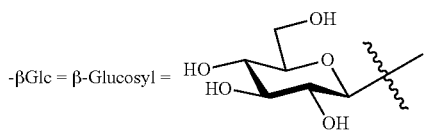

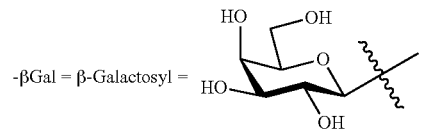

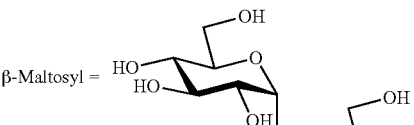

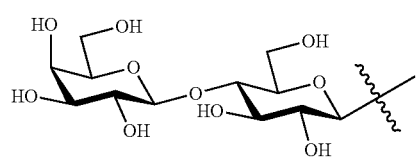

Another preferred embodiment according to the present invention is directed to a C-terminal HSP90 inhibitor of general formula (I),

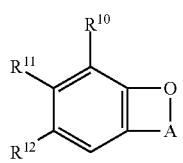

(I)

wherein

A represents

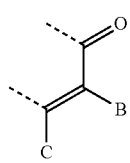

B represents —NH—C(O)—R²³, —NH—SO₂—R²³

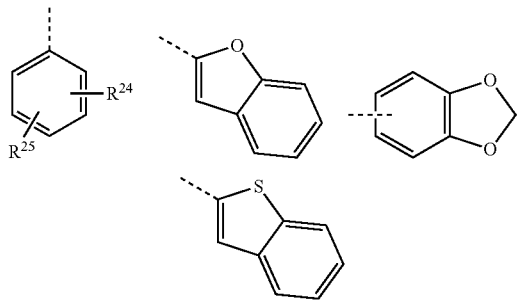

C represents —H, —OH;
R¹⁰ represents —H, —CH₃, —OCH₃, —F, —Cl, —Br, —I;
R¹¹ represents —OR²⁰, —OCH₂R¹⁹, —CO₂H, —CH₂OH, —CO₂CH₃, —NH₂, —NH—C(O)—CH₃,

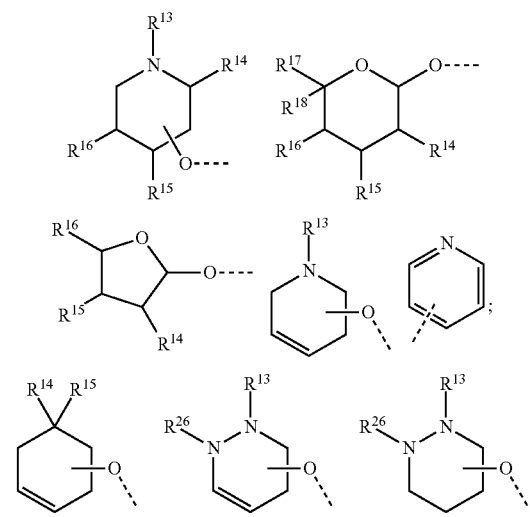

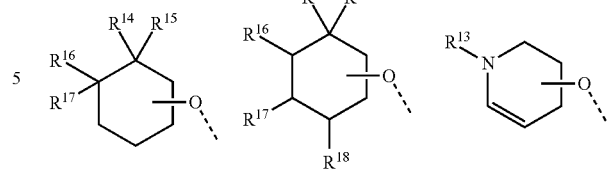

R¹² represents —H, —CH₃, —OCH₃;
R¹³ and R²⁶ are independently of each other —H, —CH₃, —C(O)CH₃;
R¹⁴, R¹⁵, R¹⁶, R¹⁷ and R¹⁸ are independently of each other selected from: —H, —OH, —NH₂, —OCH₃, —OC₂H₅, —CH₃,    —O—C(O)—NH₂,    —O—C(O)—NHR²², —C₂H₄—S(O)₂—OCH₃,    —C₂H₄—P(O)(OCH₃)₂, —CH₂—O—C(O)CH₃, —CH₂—NH—S(O)₂—OCH₃,

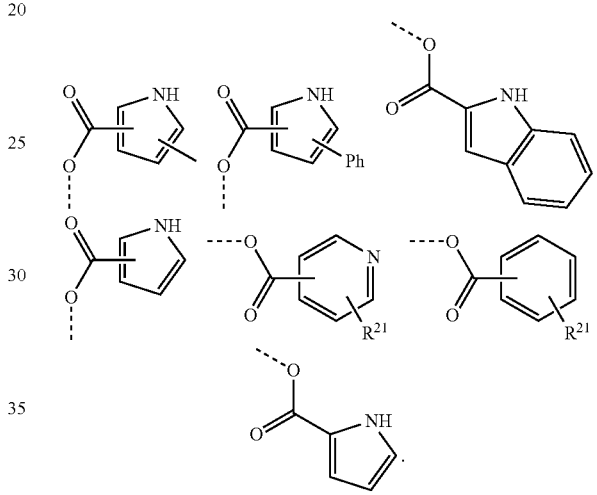

R¹⁹ represents —CH₂—NH₂, —CH₂—NHCH₃, —CH(OH)—CH₂(OH),

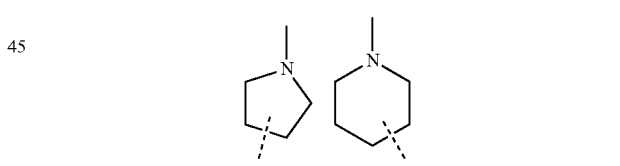

R²⁰ represents —H, —C(O)—CH₃, —C(O)—C₂H₅, —C(O)—C₃H₇,   —C(O)—NH₂,   —C(O)—NH—CH₃, —C(O)—NH—C₂H₅, —SO₂(CH₃),

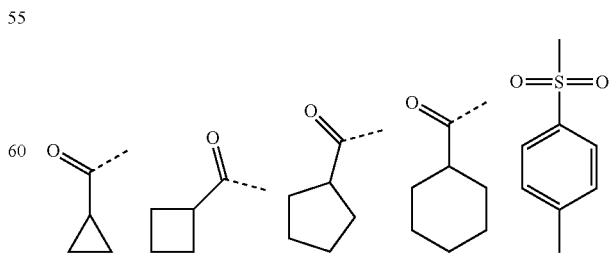

R²¹ represents —H, —OH, —SH, —CH₃, —C₂H₅, —F, —Cl, —Br, —I;

$R^{22}$ represents —CH$_3$, —C$_2$H$_5$, —C$_3$H$_7$, —C$_4$H$_9$,

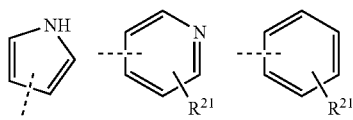

$R^{23}$ represents —CH$_3$, —C$_2$H$_5$, —C$_3$H$_7$, —C$_4$H$_9$, —CH$_2$-Ph, —C$_2$H$_4$-Ph, —O—CH$_2$-Ph,

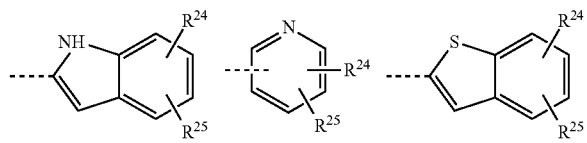

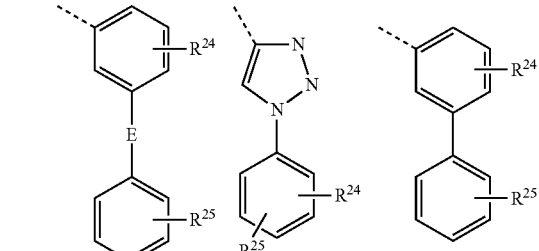

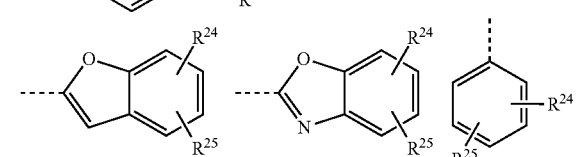

$R^{24}$ and $R^{25}$ are independently of each other selected from —H, —OH, —OCH$_3$, —OC$_2$H$_5$, —OPh, —O—CH$_2$-Ph, —CH$_2$-Ph, —C$_2$H$_4$-Ph, —NH$_2$, —NO$_2$, —CH$_2$—CH═C (CH$_3$)$_2$, —CH═CHPh, —F, —Cl, —Br, —I, —CN, —CH$_3$, —C$_2$H$_5$, —C$_3$H$_7$, —C$_4$H$_9$, —OCF$_3$, —CF$_3$, —C(CH$_3$)$_3$, -Ph, $R^{24}$ together with $R^{25}$ can form together with the 2 aromatic carbons they are connected to a cycle selected from:

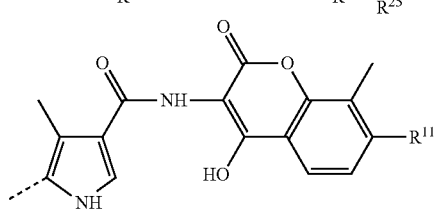

E represents —O—, —S—, —NH—, —CH$_2$—, —OCH$_2$—;

and enantiomers, stereoisomeric forms, mixtures of enantiomers, diastereomers, mixtures of diastereomers, anomers, hydrates, solvates, acid salt forms, tautomers, and racemates of the above mentioned compounds and pharmaceutically acceptable salts thereof for use in the treatment of pituitary adenoma, wherein the pituitary adenoma is selected from corticotroph adenoma, lactotroph adenoma, somatotroph adenoma and thyrotroph adenoma.

Preferred C-terminal HSP90 inhibitors according to the present invention are compounds of general formula (I):

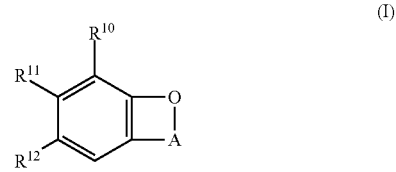

wherein

A represents

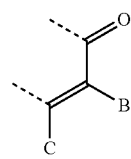

B represents —NH—C(O)—R$^{23}$, or —NH—SO$_2$—R$^{23}$

C represents —H, —OH, $R^{10}$ represents —H, —CH$_3$, —OCH$_3$, —F, —Cl, —Br, —I;

$R^{11}$ represents —OR$^{20}$, —OCH$_2$R$^{19}$,

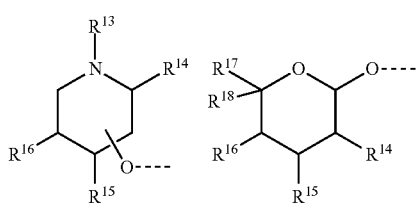

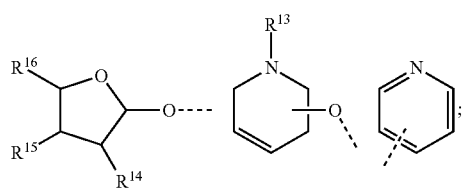

$R^{12}$ represents —H, —CH$_3$, —OCH$_3$;

and $R^{13}$, $R^{14}$, $R^{15}$, $R^{16}$, $R^{17}$, $R^{18}$ and $R^{23}$ have the meaning defined above, and enantiomers, stereoisomeric forms, mixtures of enantiomers, diastereomers, mixtures of diastereomers, anomers, hydrates, solvates, acid salt forms, tautomers, and racemates of the above mentioned compounds and pharmaceutically acceptable salts thereof for use in the treatment of pituitary adenoma, wherein the pituitary adenoma is selected from corticotroph adenoma, lactotroph adenoma, somatotroph adenoma and thyrotroph adenoma.

Preferably, R$^{23}$ is selected from:

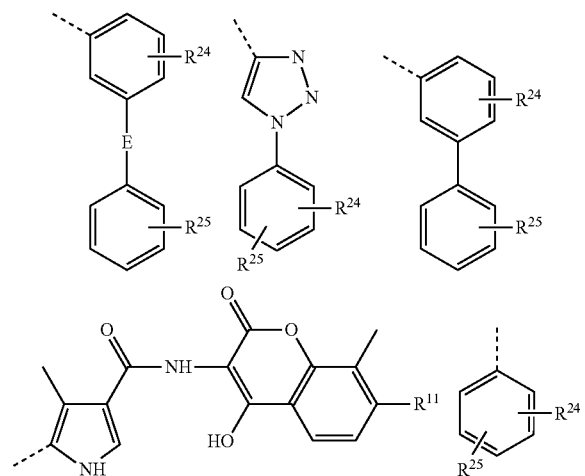

wherein R$^{11}$, R$^{24}$ and R$^{25}$ have the meanings defined above.

Another preferred embodiment is directed to compounds of general formula (I),

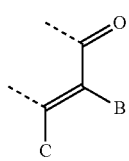 (I)

wherein
A represents

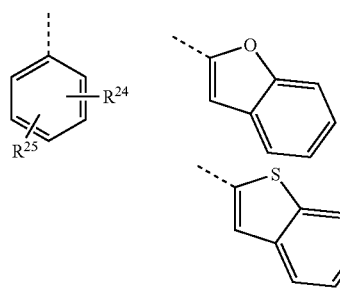

B represents

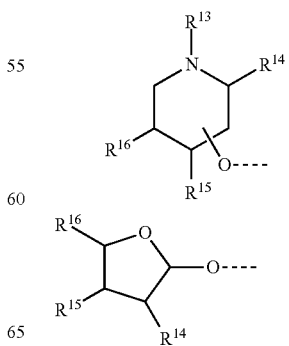

R$^{10}$ represents —H, —CH$_3$, —OCH$_3$, —F, —Cl, —Br, —I;
R$^{11}$ represents —OR$^{20}$, —OCH$_2$R$^{19}$,

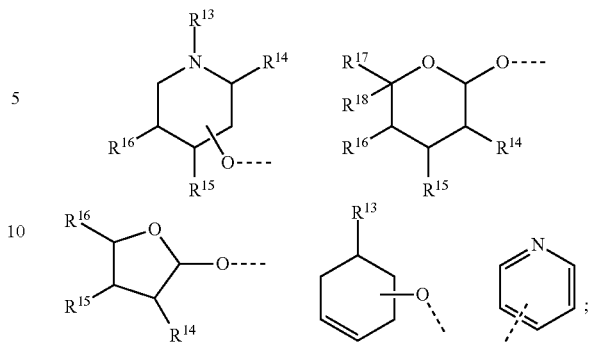

R$^{12}$ represents —H, —CH$_3$, —OCH$_3$;
and C, R$^{13}$, R$^{14}$, R$^{15}$, R$^{16}$, R$^{17}$, R$^{18}$, R$^{24}$ and R$^{25}$ have the meanings defined above, and enantiomers, stereoisomeric forms, mixtures of enantiomers, diastereomers, mixtures of diastereomers, anomers, hydrates, solvates, acid salt forms, tautomers, and racemates of the above mentioned compounds and pharmaceutically acceptable salts thereof for use in the treatment of pituitary adenoma, wherein the pituitary adenoma is selected from corticotroph adenoma, lactotroph adenoma, somatotroph adenoma and thyrotroph adenoma.

Preferred C-terminalHSP90 inhibitors are compounds of general formula (I),

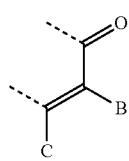 (I)

wherein
A represents

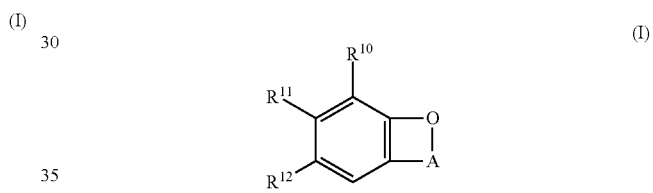

R$^{10}$ represents —H, —CH$_3$, —OCH$_3$, —F, —Cl, —Br, —I;
R$^{11}$ represents $R^{12}$ represents —H, —CH$_3$, —OCH$_3$;

and B, C, $R^{13}$, $R^{14}$, $R^{15}$, $R^{16}$, $R^{17}$ and $R^{18}$ have the meanings defined above, and enantiomers, stereoisomeric forms, mixtures of enantiomers, diastereomers, mixtures of diastereomers, anomers, hydrates, solvates, acid salt forms, tautomers, and racemates of the above mentioned compounds and pharmaceutically acceptable salts thereof for use in the treatment of pituitary adenoma, wherein the pituitary adenoma is selected from corticotroph adenoma, lactotroph adenoma, somatotroph adenoma and thyrotroph adenoma.

Particularly preferred C-terminal HSP90 inhibitors are compounds of general formula (I)

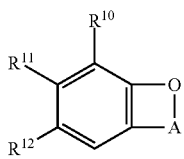

(I)

wherein

A represents

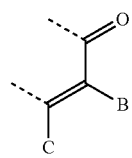

$R^{10}$ represents —H, —CH$_3$, —OCH$_3$, —F, —Cl, —Br, —I;

$R^{11}$ represents

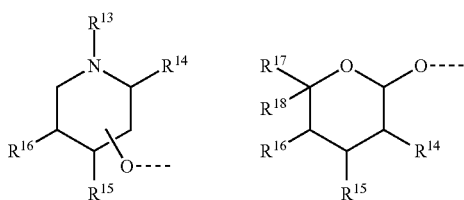

$R^{12}$ represents —H, —CH$_3$, —OCH$_3$;

$R^{13}$ represents —H, —CH$_3$, —C(O)CH$_3$;

$R^{14}$, $R^{15}$, $R^{16}$, $R^{17}$ and $R^{18}$ are independently of each other selected from: —H, —OH, —OCH$_3$, —CH$_3$, —O—C(O)—NH$_2$, —O—C(O)—NHR$^{22}$;

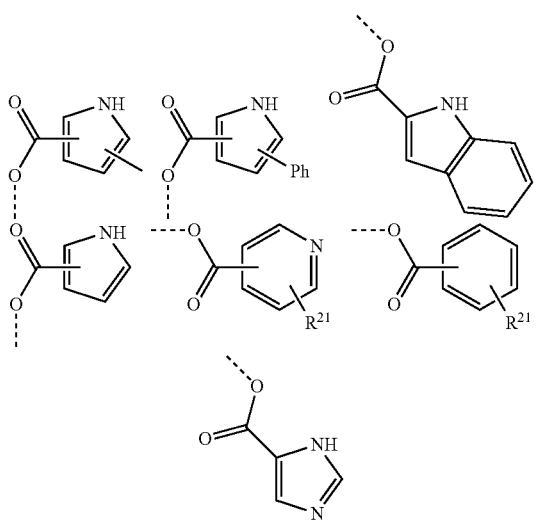

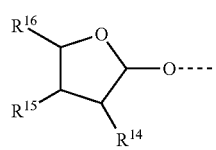

wherein B, C, $R^{21}$ and $R^{22}$ are defined as above, and enantiomers, stereoisomeric forms, mixtures of enantiomers, diastereomers, mixtures of diastereomers, anomers, hydrates, solvates, acid salt forms, tautomers, and racemates of the above mentioned compounds and pharmaceutically acceptable salts thereof for use in the treatment of pituitary adenoma, wherein the pituitary adenoma is selected from corticotroph adenoma, lactotroph adenoma, somatotroph adenoma and thyrotroph adenoma.

Further embodiment of the present invention is directed to the use of at least one C-terminal HSP90 inhibitor of general formula (I), (II) or (III) in the manufacture of a medicament for the treatment of pituitary adenoma, wherein the pituitary adenoma is selected from corticotroph adenoma, lactotroph adenoma, somatotroph adenoma and thyrotroph adenoma.

The pituitary adenoma of the present invention may be selected from the group comprising or consisting of: corticotroph adenomas (also called ACTH-secreting pituitary adenomas, Cushing's disease or pituitary-dependent Cushing's syndrome), lactotroph adenomas, somatotroph adenomas, thyrotroph adenomas, gonadotrophic adenomas. Among them, corticotroph pituitary adenomas are especially preferred.

Another embodiment of the present invention is a combination of at least one C-terminal HSP90 inhibitor, such as a C-terminal HSP90 inhibitor of general formula (I), (II) or (III) and at least one other active agent for use in the treatment of pituitary adenoma, wherein the pituitary adenoma is selected from corticotroph adenoma, lactotroph adenoma, somatotroph adenoma and thyrotroph adenoma.

In said combination the at least one active agent for use in the treatment of pituitary adenomas is preferably selected from the group comprising or consisting of ketoconazole, octreotide, pasireotide, mifepristone, retinoic acid, rosiglitazone, cabergoline and bromocriptine.

Further embodiment of the present invention is directed to the use of said combination of at least one C-terminal HSP90 inhibitor of general formula (I), (II) or (III) and at least one other active agent in the manufacture of a medicament for the treatment of pituitary adenoma, wherein the pituitary adenoma is selected from corticotroph adenoma, lactotroph adenoma, somatotroph adenoma and thyrotroph adenoma.

In other embodiment of the present invention pharmaceutical composition comprises at least one C-terminal HSP90 inhibitor of general formula (I), (II), or (III) as an active agent, together with at least one other active agent, carrier, excipient and/or diluent.

Preferred pharmaceutical compositions comprise at least one other active agent, which is selected from the group comprising or consisting of ketoconazole, octreotide, pasireotide, mifepristone, retinoic acid, rosiglitazone, cabergoline and bromocriptine.

Said pharmaceutical composition is suitable for use in the treatment of pituitary adenoma, wherein the pituitary adenoma is selected from corticotroph adenoma, lactotroph adenoma, somatotroph adenoma and thyrotroph adenoma.

The further embodiment of the present invention is a plant extract from *Silybum marianum* containing at least one C-terminal HSP90 inhibitor, such as a C-terminal HSP90 inhibitor of general formula (II) or (III) for use in the treatment of pituitary adenomas, wherein the pituitary adenomas are selected from corticotroph adenomas, lactotroph adenomas, somatotroph adenomas and thyrotroph adenomas. One known extract used in medicine is silymarin; a flavonolignane complex consisting of silibinin A and B/silybin/silymarin I, isosilibinin A and B, silicristin/silymarin II, and silidianin.

HSP90 (heat shock protein 90) is a molecular chaperone and is one of the most abundant proteins expressed in cells. It is a member of the heat shock protein family, which is up-regulated in response to stress.

Heat shock proteins, as a class, are among the most highly expressed cellular proteins across all species. As their name implies, heat shock proteins protect cells when stressed by elevated temperatures. They account for 1-2% of total protein in unstressed cells. However when cells are heated, the fraction of heat shock proteins increases to 4-6% of cellular proteins. HSP90 is one of the most common of the heat-related proteins. The "90" comes from the fact that it weighs roughly 90 kDa.

In humans, Hsp90 exists as a homodimer and consists of three highly conserved domains: a highly conserved N-terminal domain (NTD) of 25 kDa (amino acids 9 to 232 in the human HSP90-alpha sequence), a middle domain (MD) of 35 kDa and a C-terminal domain (CTD) of 12 kDa (amino acids 629 to 731 in the human HSP90-alpha sequence).

N-Terminal domain shows high homology not only among members of the Hsp90 chaperone family, but also to members of the ATPase/kinase GHKL (Gyrase, Hsp90, Histidine Kinase, MutL) superfamily. The N-terminal domain contains an ATP-binding site that also binds the natural products, geldanamycin (GDA) and radicicol. Some Hsp90 functions depend upon the ability of the N-terminal domain to bind and hydrolyze ATP.

The middle domain exhibits high affinity for co-chaperones as well as client proteins. Structural and functional analyses have demonstrated that the middle domain of Hsp90 contains a catalytic loop, which may serve as an acceptor for the γ-phosphate of ATP, when it is bound to the N-terminus.

The C-Terminal domain has a second ATP-binding site. The Hsp90 C-terminal domain is known to display chaperone activity independent of the N-terminus, as well as mediate dimerization and oligomerization of Hsp90 monomeric species. Structurally, the C-terminus of Hsp90 contains a conserved pentapeptide sequence (Met-Glu-Glu-Val-Asp) that is recognized by co-chaperones. The co-chaperones that recognize this sequence all contain multiple copies of the tetratricopeptide repeat (TPR), a 34 amino acid sequence that elicits specific binding to Hsp90. This sequence, though conserved, has been reported as dispensable for activity.

The functions of HSP90 include assisting in protein folding, stabilizing various proteins such as steroid receptors, and aiding in protein degradation. To date, more than 200 HSP90-dependent client proteins have been discovered, of which HER2, Src family kinases, Raf, PLK, RIP, Akt, telomerase and Met are directly associated with the six hallmarks of cancer. Consequently, inhibition of the HSP90 folding machinery provides a combinatorial approach towards the disruption of multiple signaling nodes that are critical for malignant cell growth and proliferation. That is why HSP90 inhibitors are investigated as anti-cancer drugs.

Inhibitors of the chaperone protein Hsp90 have been found to have effects in HER2-positive metastatic breast cancer, multiple myeloma, leukemia, and non-small-cell lung cancer (Trepel et al. Nature Reviews Cancer 10:537-549, 2010). However, these compounds were not efficacious in, for example, prostate cancer (Heath E. I. et al., Clinical Cancer Research 14:7940-7946). Therefore, no prediction can be made a priori about the effects of HSP90 inhibitors on other tumor types.

HSP90 inhibitors belong to two clearly defined groups: the ones that bind to the N-terminal domain (amino acids 9 to 232 in the human HSP90-alpha sequence), and the ones that bind to the C-terminal domain (amino acids 629 to 731 in the human HSP90-alpha sequence; Whitesell L. and Lindquist SL. Nature Reviews Cancer 5:761-772, 2005; Zhang H. and Burrows F. Journal of Molecular Medicine 82:488-499, 2004). Among the first group are ansamycin derivatives such as geldanamycin, 17-AAG, and 17-DMAG; macrolides such as radicicol, and purine derivatives such as CCT018159.

The term "C-terminal HSP90 inhibitor" as used herein refers to all inhibitors of HSP90, which bind to the C-terminal domain of HSP90. In addition, C-terminal HSP90 inhibitors induce a distinct conformation of HSP90 that alters HSP90 dimerization and client interactions. Among the C-terminal HSP90 inhibitors novobiocin, silibinin (also called silybin), and their derivatives (Yun B-G, et al., Biochemistry 43:8217-8229, 2004; Kusuma B. R. et al., Bioorganic & Medicinal Chemistry Letters 21:7170-7174, 2011; Kusuma B. R. et al., J. Med. Chem. 55:5797-5812, 2012; Eskew J. D. et al., BMC Cancer 11:468, 2011; Cohen S. M. et al., Ann. Surg. Oncol. 19:S483-S490, 2012; Zhao H. et al., Bioorganic & Medicinal Chemistry Letters 21:2659-2664, 2011) are especially preferred.

Therefore, one aspect of the present invention refers to C-terminal HSP90 inhibitors such as silibinin and novobiocin for the use in treatment of pituitary adenomas, such as corticotroph adenomas, lactotroph adenomas, somatotroph adenomas and thyrotroph adenomas.

Silibinin, also known as silybin or silibin, is the major active constituent of silymarin, a standardized extract of the *Silybum marianum* (also called milk thistle) seeds containing mixture of flavonolignans consisting of among others of silibinin, isosilibinin, silicristin and silidianin. Silibinin itself is mixture of two diastereomers silibinin A and silibinin B in approximately equimolar ratio (scheme 1). The IUPAC name of silibinin is (2R,3R)-3,5,7-trihydroxy-2-[(2R,3R)-3-(4-hydroxy-3-methoxyphenyl)-2-(hydroxymethyl)-2,3-dihydrobenzo[b][1,4]dioxin-6-yl]chroman-4-one. Hydroxy groups of silibinin can be easily acetylated or glycosylated, for example, with glucose, galactose, maltose and lactose.

Generally, an extract of *Silybum marianum* has the main active flavonoids, i.e. silybin, isosilybin, silychristin, silydianin and taxifolin. The maximum yields of taxifolin, silychristin, silydianin, silibinin A and silibinin B in ethanol were 0.6, 4.0, 0.4, 4.0 and 7.0 mg/g of defatted seed, respectively. If silibinin A is the diastereoisomer of choice methanol would be the preferred extraction solvent because it yields the highest silibinin A to silibinin B ratio. Lipid removal is an important extraction step, because defatted material yields twice the silymarin concentration. As an alternative extraction solvent hot water can be used. Silymarin isolated from *Silybum marianum*, is a mixture of three isomers: silybin, silydianin and silychristin.

Scheme 1. Structure of silibinin A and silibinin B

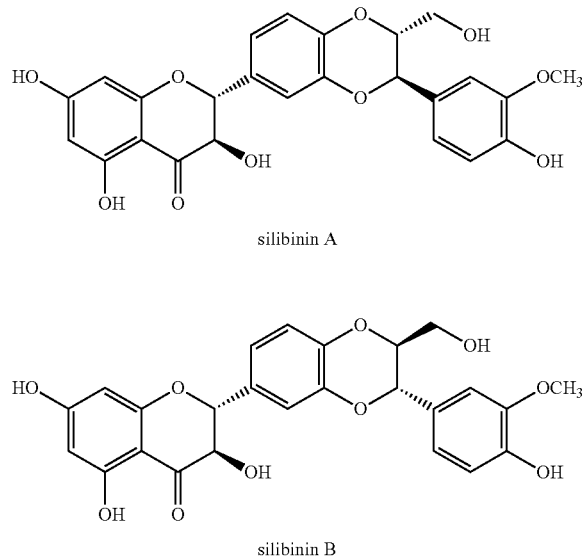

silibinin A silibinin B

Silibinin has shown effects in some animal models of prostate cancer, pancreas carcinoma, hepatocellular carcinoma, cervical cancer, and skin tumors (Gazák R. et al., Current Medicinal Chemistry 14:315-338, 2007). It might also be useful for the prevention of the development of bladder tumors. However, it did not show therapeutic effects in some models of pulmonary adenoma. Therefore, no prediction can be made a priori about the effects of silibinin on other tumor types.

Silibinin has been found to modulate in vitro glucocorticoid secretion in adrenal tumor cells (also called Cushing's syndrome but clearly different from pituitary-derived Cushing's disease or corticotroph adenoma). However, in adrenal cells, silibinin potentiates the effects of ACTH (Rácz K. et al., J Endocrinol. 124:341-5, 1990). This effect would not be desirable in patients with corticotroph adenomas that secrete abnormally high levels of ACTH. Therefore, the person skilled in the art would assume that silibinin would have a detrimental effect on patients with corticotroph adenomas instead of the desired therapeutic effect that would rather involve the inhibition of ACTH and its effects.

Novobiocin, also known as albamycin or cathomycin, is an aminocoumarin antibiotic that is produced by the actinomycete *Streptomyces niveus*. The IUPACname of novobiocin is: 4-Hydroxy-3-[4-hydroxy-3-(3-methylbut-2-enyl)benzamido]-8-methylcoumarin-7-yl 3-O-carbamoyl-5,5-di-C-methyl-α-L-lyxofuranoside and the structural chemical formula is as follows:

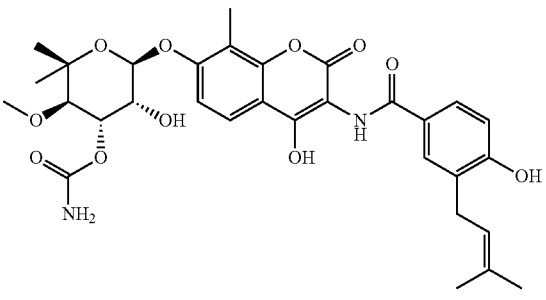

Novobiocin

Surprisingly, it was found that HSP90 protein is highly expressed in human corticotroph adenomas in comparison to normal pituitary gland (see FIG. 1). HSP90 inhibitors have anti-proliferative effects in other tumor types that express HSP90. Therefore, based on this new protein expression results, it is predicted that HSP90 inhibitors would reduce the proliferation of pituitary tumor cells, in particular the proliferation of corticotroph adenomas, lactotroph adenomas, somatotroph adenomas and thyrotroph adenomas. In fact, the present invention discloses that the HSP90 inhibitors 17-AAG, silibinin, and novobiocin strongly inhibit the proliferation of the corticotroph tumor cell line AtT-20 (see FIG. 2). One preferred embodiment is therefore a C-terminal HSP90 inhibitor for use in the treatment of corticotroph adenoma.

Surprisingly, only the HSP90 inhibitors that bind to the N-terminal domain such as 17-AAG induced the degradation of the GR (glucocorticoid receptor) protein, while C-terminal HSP90 inhibitors such as novobiocin and silibinin did not produce this effect (see FIG. 3). In addition, only novobiocin and silibinin increased the transcriptional activity of GR, whereas 17-AAG inhibited this activity (see FIG. 4).

These results show for the first time a sharp contrast between N-terminal and C-terminal HSP90 inhibitors as regards their effects on GR stability and activity, which is particularly relevant for the treatment of Cushing's disease that presents high glucocorticoid levels and partial glucocorticoid resistance.

To mimic the high levels of the glucocorticoid cortisol that is present in patients with Cushing's disease, AtT-20 cells were incubated in the presence of the synthetic glucocorticoid dexamethasone. Under these conditions, only silibinin reduced ACTH production, while 17-AAG had no effect (see FIG. 5), which is in line with our observation of higher GR activity only under silibinin treatment. Silibinin also increases the inhibition of ACTH secretion produced by sub-optimal concentrations of the somatostatin analog octreotide in AtT-20 cells (see FIG. 6).

The present invention is based on the findings that only C-terminal HSP90 inhibitors such as silibinin, novobiocin, and their derivates can reduce ACTH in patients with Cushing's disease, but not the conventional N-terminal HSP90 inhibitors such as 17-AAG.

Furthermore, *Silibum marianum* extract (source: Silicur from Hexal, Germany containing 108.2 mg of Silibinin per capsule) inhibited the growth of corticotroph adenomas (see FIG. 7) and decreased the plasma ACTH (see FIG. 8) and plasma corticosterone (see FIG. 9) in nude mice having xenografts of AtT-20 corticotroph adenomas.

In addition, silibinin proved efficient in inhibiting prolactin secretion in GH3 prolactinoma cells (see FIG. 10) and growth hormone secretion in GH3 somatotroph adenoma cells (see FIG. 11) without inducing any toxicity to the GH3 cells.

These results could not have been predicted based on the previously known effects of conventional HSP90 inhibitors on other tumor types. Based on these surprising effects, it is clear that C-terminal HSP90 inhibitors, in particular substances of the silibinin and novobiocin families as represented by the compounds of general formula (I), (II), (III) can be used to treat pituitary tumors, preferably corticotroph adenomas, lactotroph adenomas, somatotroph adenomas and thyrotroph adenomas, and more preferably Cushing's disease, in human patients, dogs, and horses.

Furthermore, a combination of at least one C-terminal HSP90 inhibitor of general formula (I), (II) or (III) and at least one other active agent can be used for the treatment of pituitary adenoma, wherein the pituitary adenoma is selected from corticotroph adenoma, lactotroph adenoma, somatotroph adenoma and thyrotroph adenoma.

It is preferred that in said combination the at least one other active agent for the treatment of pituitary adenomas is selected from the group comprising or consisting of ketoconazole, somatostatin, analogues of somatostatin, octreotide, pasireotide, lanreotide, vapreotide, GR antagonists like mifepristone, retinoic acid, rosiglitazone, and dopamine agonists like cabergoline and bromocriptine.

Pharmaceutical Compositions

The present invention also comprises pharmaceutically acceptable salts of C-terminal HSP90 inhibitors, including C-terminal HSP90 inhibitors according to the general formula (I), (II) or (III), all stereoisomeric forms of C-terminal HSP90 inhibitors, including C-terminal HSP90 inhibitors according to the general formula (I), (II), or (III) as well as solvates, especially hydrates or prodrugs thereof.

The C-terminal HSP90 inhibitors, including C-terminal HSP90 inhibitors of general formula (I), (II), or (III) of the present invention may form salts with organic or inorganic acids or bases. Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

In the case the inventive C-terminal HSP90 inhibitors, including C-terminal HSP90 inhibitors of the general formula (I), (II) or (III) bear acidic groups, salts could also be formed with inorganic or organic bases. Examples for suitable inorganic or organic bases are, for example NaOH, KOH, NH$_4$OH, tetraalkylammonium hydroxide, lysine or arginine and the like. Salts may be prepared in a conventional manner using methods well known in the art, for example by treatment of a solution of the compound of the general formula (I), (II) or (III) with a solution of an acid, selected out of the group mentioned above.

Some of the C-terminal HSP90 inhibitors, including some of the C-terminal HSP90 inhibitors of the general formula (I), (II) or (III) of the present invention may be crystallised or recrystallised from solvents such as aqueous and organic solvents. In such cases solvates may be formed. This invention includes within its scope stoechiometric solvates including hydrates, as well as C-terminal HSP90 inhibitors (I), (II) or (III) containing variable amounts of water that may be produced by processes such as lyophilisation.

The C-terminal HSP90 inhibitors, including the C-terminal inhibitors of the general formula (I), (II) or (III) exist in the form of optical isomers, i.e. enantiomers and mixtures of said isomers in all ratios, e.g. racemic mixtures. The invention includes all such forms, in particular the pure isomeric forms or enantiomeric forms. The different isomeric forms may be separated or resolved one from the other by conventional methods, or any given isomer may be obtained by conventional synthetic methods or by stereospecific or asymmetric syntheses. Where a C-terminal HSP90 inhibitor according to the general formula (I), (II) or (III) contains an alkene moiety, the alkene can be presented as a cis or trans isomer or a mixture thereof. When an isomeric form of a compound of the invention is provided substantially free of other isomers, it will preferably contain less than 5% w/w, more preferably less than 2% w/w and especially less than 1% w/w of the other isomer(s).

Surprisingly, it was found that C-terminal HSP90 inhibitors, including C-terminal HSP90 inhibitors of general formula (I), (II) or (III) as well as the pharmaceutical compositions comprising said compounds are useful for the treatment of pituitary adenoma, and in particular for the pituitary adenomas that are secreting hormones. Thus, C-terminal HSP90 inhibitors, including the C-terminal HSP90 inhibitors according to the general formula (I), (II) or (III) of the present invention can be used for treatment of pituitary adenomas or for the preparation of a pharmaceutical formulation for prophylaxis and treatment of pituitary adenoma, wherein the pituitary adenoma is selected from corticotroph adenoma, lactotroph adenoma, somatotroph adenoma and thyrotroph adenoma. Therefore, another aspect of the present invention is directed to pharmaceutical compositions comprising at least one C-terminal HSP90 inhibitor according to the general formula (I), (II) or (III) of the present invention as active ingredient, together with at least one other active agent, carrier, excipient and/or diluents.

In said compositions the at least one other active agent is preferably selected from the group comprising or consisting of ketoconazole, somatostatin analogs like somatostatin, octreotide, pasireotide, lanreotide, vapreotide, GR antagonists like mifepristone, retinoic acid, rosiglitazone, and dopamine agonists like cabergoline or bromocriptine.

Preferred, in said compositions the at least one other active agent is selected from the group comprising or consisting of ketoconazole, octreotide, pasireotide, mifepristone, retinoic acid, rosiglitazone, cabergoline or bromocriptine.

The pharmaceutical compositions of the present invention can be prepared in a conventional solid or liquid carrier or diluent and a conventional pharmaceutically-made adjuvant at suitable dosage level in a known way. The preferred preparations are adapted for oral application. These administration forms include, for example, pills, tablets, film tablets, coated tablets, capsules, powders and deposits.

Furthermore, the present invention also includes pharmaceutical preparations for parenteral application, including dermal, intradermal, intragastral, intracutan, intravasal, intravenous, intramuscular, intraperitoneal, intranasal, intravaginal, intrabuccal, percutan, rectal, subcutaneous, sublingual, topical, or transdermal application, which preparations in addition to typical vehicles and/or diluents contain at least one C-terminal HSP90 inhibitor according to the general formula (I), (II) or (III) and/or a pharmaceutical acceptable salt thereof as active ingredient for use in the treatment of pituitary adenoma, wherein the pituitary adenoma is selected from corticotroph adenoma, lactotroph adenoma, somatotroph adenoma and thyrotroph adenoma.

The pharmaceutical compositions according to the present invention containing at least one C-terminal HSP90 inhibitor according to the general formula (I), (II) or (III) and/or a pharmaceutical acceptable salt thereof as active ingredient will typically be administered together with suitable carrier materials selected with respect to the intended form of administration, i.e. for oral administration in the form of tablets, capsules (either solid filled, semi-solid filled or liquid filled), powders for constitution, extrudates, deposits, gels, elixirs, dispersable granules, syrups, suspensions, and the like, and consistent with conventional pharmaceutical practices. For example, for oral administration in the form of tablets or capsules, the active drug component may be combined with any oral non-toxic pharmaceutically acceptable carrier, preferably with an inert carrier like lactose, starch, sucrose, cellulose, magnesium stearate, dicalcium phosphate, calcium sulfate, talc, mannitol, ethyl alcohol (liquid filled capsules) and the like. Moreover, suitable binders, lubricants, disintegrating agents and colouring agents may also be incorporated into the tablet or capsule. Powders and tablets may contain about 5 to about 95 weight % of the C-terminal HSP90 inhibitor (I), (II) or (III) and/or the respective pharmaceutically active salt as active ingredient.

Suitable binders include starch, gelatin, natural sugars, corn sweeteners, natural and synthetic gums such as acacia, sodium alginate, carboxymethylcellulose, polyethylene glycol and waxes. Among suitable lubricants there may be mentioned boric acid, sodium benzoate, sodium acetate, sodium chloride, and the like. Suitable disintegrants include starch, methylcellulose, guar gum, and the like. Sweetening and flavouring agents as well as preservatives may also be included, where appropriate. The disintegrants, diluents, lubricants, binders etc. are discussed in more detail below.

Moreover, the pharmaceutical compositions may be formulated in sustained release form to provide the rate controlled release of any one or more of the components or active ingredients to optimise the therapeutic effect(s), e.g. antihistaminic activity and the like. Suitable dosage forms for sustained release include tablets having layers of varying disintegration rates or controlled release polymeric matrices impregnated with the active components and shaped in tablet form or capsules containing such impregnated or encapsulated porous polymeric matrices.

Liquid form preparations include solutions, suspensions, and emulsions. As an example, there may be mentioned water or water/propylene glycol solutions for parenteral injections or addition of sweeteners and opacifiers for oral solutions, suspensions, and emulsions. Liquid form preparations may also include solutions for intranasal administration. Aerosol preparations suitable for inhalation may include solutions and solids in powder form, which may be present in combination with a pharmaceutically acceptable carrier such as an inert, compressed gas, e.g. nitrogen. For preparing suppositories, a low melting fat or wax, such as a mixture of fatty acid glycerides like cocoa butter Is melted first, and the active ingredient is then dispersed homogeneously therein e.g. by stirring. The molten, homogeneous mixture is then poured into conveniently sized moulds, allowed to cool, and thereby solidified.

Also included are solid form preparations which are intended to be converted, shortly before use, to liquid form preparations for either oral or parenteral administration. Such liquid forms include solutions, suspensions, and emulsions.

The C-terminal HSP90 inhibitors according to the general formula (I), (II) or (III) may also be delivered transdermally. The transdermal compositions may have the form of a cream, a lotion, an aerosol and/or an emulsion and may be included in a transdermal patch of the matrix or reservoir type as is known in the art for this purpose.

The term capsule as recited herein refers to a specific container or enclosure made e.g. of methyl cellulose, polyvinyl alcohols, or denatured gelatins or starch for holding or containing compositions comprising the active ingredient (s). Capsules with hard shells are typically made of blended of relatively high gel strength gelatins from bones or pork skin. The capsule itself may contain small amounts of dyes, opaquing agents, plasticisers and/or preservatives. Under tablet a compressed or moulded solid dosage form is understood, which comprises the active ingredients with suitable diluents. The tablet may be prepared by compression of mixtures or granulations obtained by wet granulation, dry granulation, or by compaction well known to a person of ordinary skill in the art.

Oral gels refer to the active ingredients dispersed or solubilised in a hydrophilic semi-solid matrix. Powders for constitution refers to powder blends containing the active ingredients and suitable diluents, which can be suspended e.g. in water or in juice.

Suitable diluents are substances that usually make up the major portion of the composition or dosage form. Suitable diluents include sugars such as lactose, sucrose, mannitol, and sorbitol, starches derived from wheat, corn rice, and potato, and celluloses such as microcrystalline cellulose. The amount of diluent in the composition can range from about 5 to about 95% by weight of the total composition, preferably from about 25 to about 75 weight %, and more preferably from about 30 to about 60 weight %.

The term disintegrants refers to materials added to the composition to support break apart (disintegrate) and release the pharmaceutically active ingredients of a medicament. Suitable disintegrants include starches, "cold water soluble" modified starches such as sodium carboxymethyl starch, natural and synthetic gums such as locust bean, karaya, guar, tragacanth and agar, cellulose derivatives such as methylcellulose and sodium carboxymethylcellulose, microcrystalline celluloses, and cross-linked microcrystalline celluloses such as sodium croscaramellose, alginates such as alginic acid and sodium alginate, clays such as bentonites, and effervescent mixtures. The amount of disintegrant in the composition may range from about 2 to about 20 weight % of the composition, more preferably from about 5 to about 10 weight %.

Binders are substances, which bind or "glue" together powder particles and make them cohesive by forming granules, thus serving as the "adhesive" in the formulation. Binders add cohesive strength already available in the diluent or bulking agent. Suitable binders include sugars such as sucrose, starches derived from wheat corn rice and potato, natural gums such as acacia, gelatin and tragacanth, derivatives of seaweed such as alginic acid, sodium alginate and ammonium calcium alginate, cellulose materials such as methylcellulose, sodium carboxymethylcellulose and hydroxypropylmethylcellulose, polyvinylpyrrolidone, and inorganic compounds such as magnesium aluminum silicate. The amount of binder in the composition may range from about 2 to about 20 weight % of the composition, preferably from about 3 to about 10 weight %, and more preferably from about 3 to about 6 weight %.

Lubricants refer to a class of substances, which are added to the dosage form to enable the tablet granules etc. after being compressed to release from the mould or die by reducing friction or wear. Suitable lubricants include metallic stearates, such as magnesium stearate, calcium stearate, or potassium stearate, stearic acid, high melting point waxes, and other water soluble lubricants such as sodium chloride, sodium benzoate, sodium acetate, sodium oleate, polyethylene glycols and D,L-leucine. Lubricants are usually added at the very last step before compression, since they must be present at the surface of the granules. The amount of lubricant in the composition may range from about 0.2 to about 5 weight % of the composition, preferably from about 0.5 to about 2 weight %, and more preferably from about 0.3 to about 1.5 weight % of the composition.

Glidents are materials that prevent caking of the components of the pharmaceutical composition and improve the flow characteristics of granulate so that flow is smooth and uniform. Suitable glidents include silicon dioxide and talc. The amount of glident in the composition may range from about 0.1 to about 5 weight % of the final composition, preferably from about 0.5 to about 2 weight %.

Coloring agents are excipients that provide colouration to the composition or the dosage form. Such excipients can include food grade dyes adsorbed onto a suitable adsorbent such as clay or aluminum oxide. The amount of the colouring agent may vary from about 0.1 to about 5 weight % of the composition, preferably from about 0.1 to about 1 weight %.

Figure 1A:
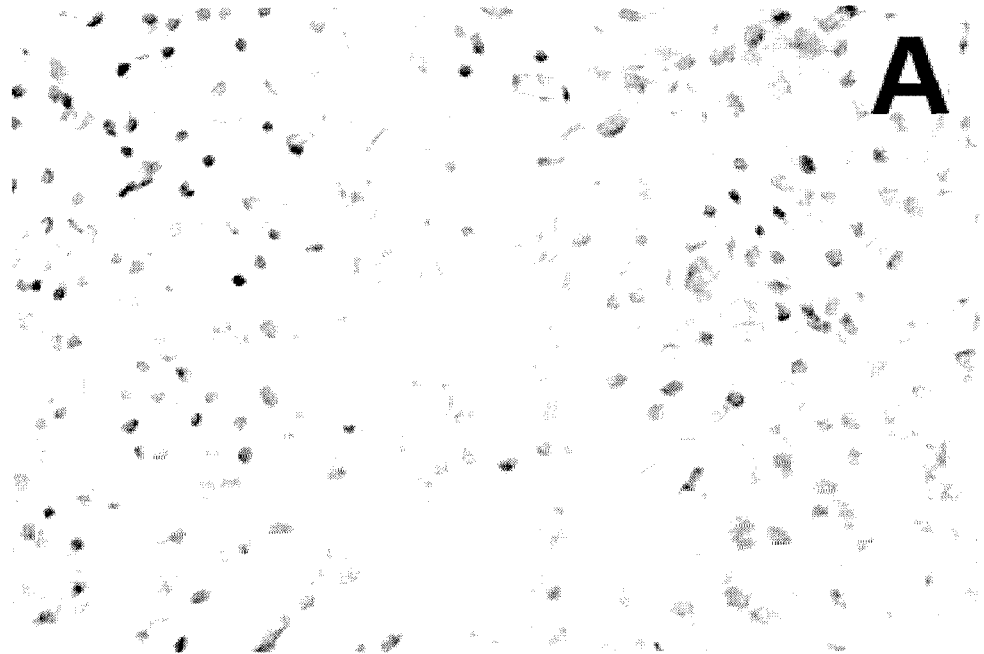
FIG. 1: HSP90 protein expression detected by immunohistochemistry. A. representative example of human normal pituitary tissue (n=6) shows only nuclear counterstaining. B. representative example of corticotroph adenoma (n=14) shows a dark cytoplasmic signal (arrows) that indicates high HSP90 expression.
Figure 1B:
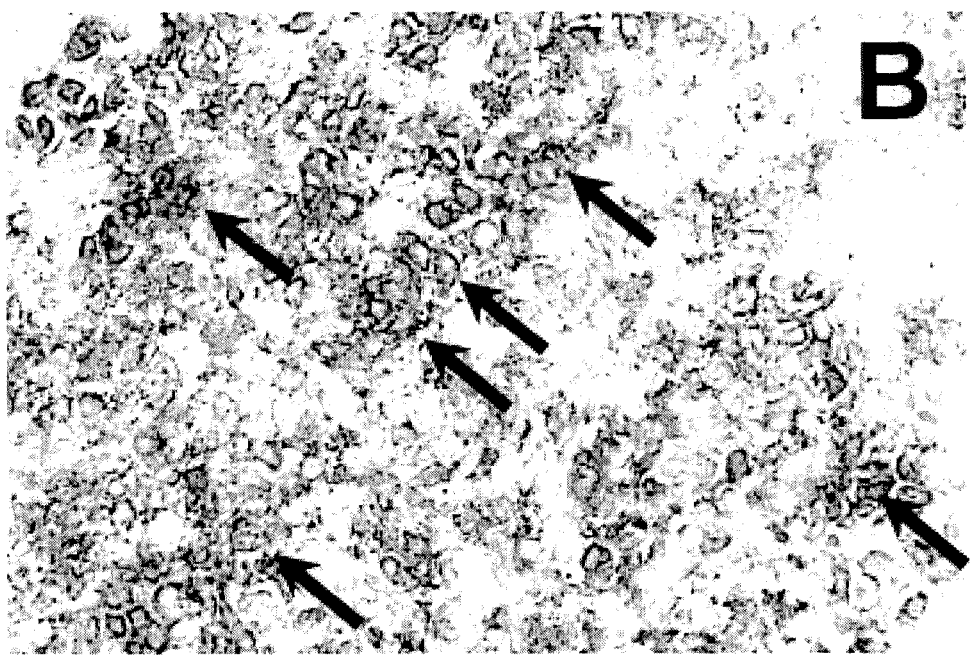
Figure 2:
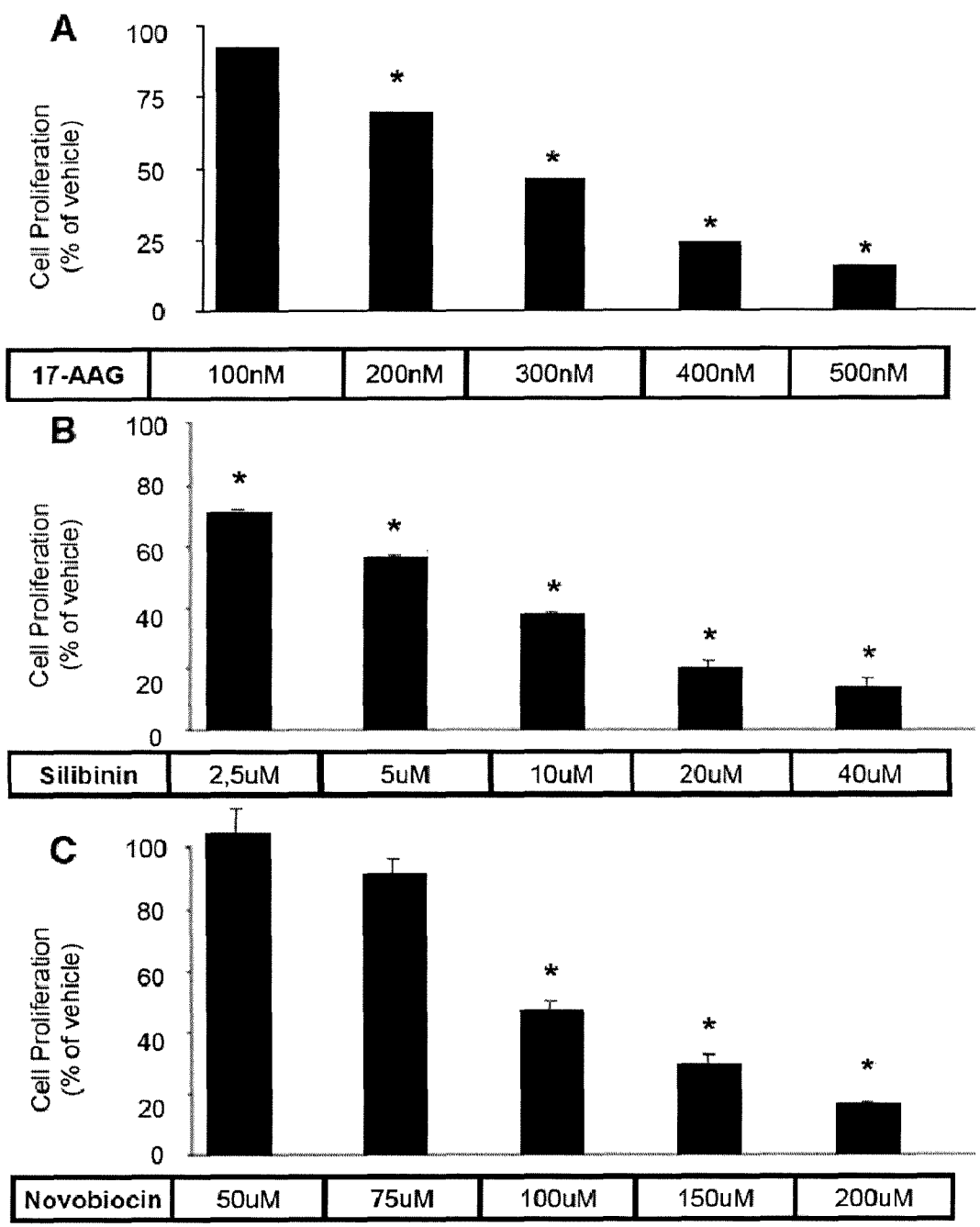
FIG. 2: HSP90 inhibitors reduce the proliferation of corticotroph adenoma cells. AtT-20 cells were treated for 96 hours with different doses of (A) 17-AAG, (B) silibinin, or (C) novobiocin. At the end of the treatment, cell proliferation was measured with the WST-1 assay. *, $p<0.01$ as compared to the vehicle, which was considered as 100%.
Figure 3:
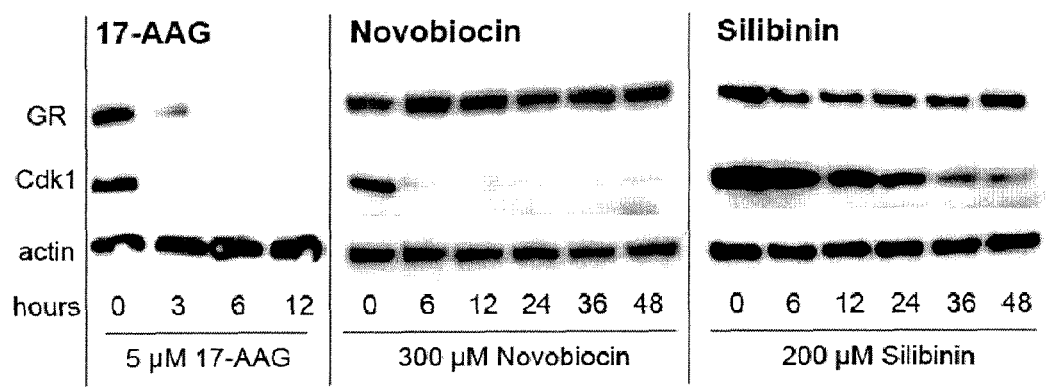
FIG. 3: N-terminal HSP90 inhibitors induce GR degradation. AtT-20 cells were treated with (A) 17-AAG, (B) silibinin, or (C) novobiocin. At the end of the treatment, the GR, Cdk1 and actin proteins were detected by Western blot. The three substances induce degradation of Cdk1, while only the N-terminal HSP90 inhibitor 17-AAG induces GR degradation.
Figure 4A:
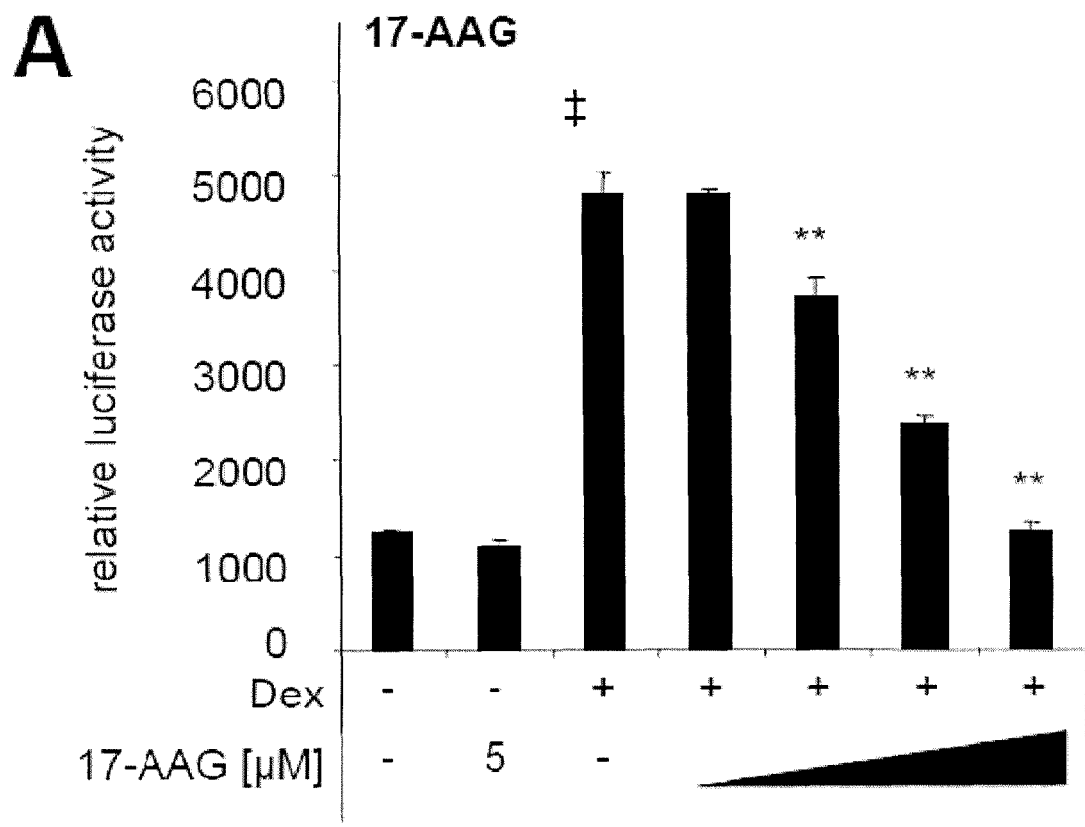
FIG. 4: C-terminal HSP90 inhibitors increase GR activity in corticotroph adenoma cells. AtT-20 cells were treated for 72 hours with different doses of (A) 17-AAG, (B) silibinin, or (C) novobiocin. At the end of the treatment, GR activity was measured by transfection of the reporter construct MTV-luc. Triangles indicate increasing concentrations of the correspondent HSP90 inhibitor. *, $p<0.01$ as compared to the vehicle.
Figure 4B:
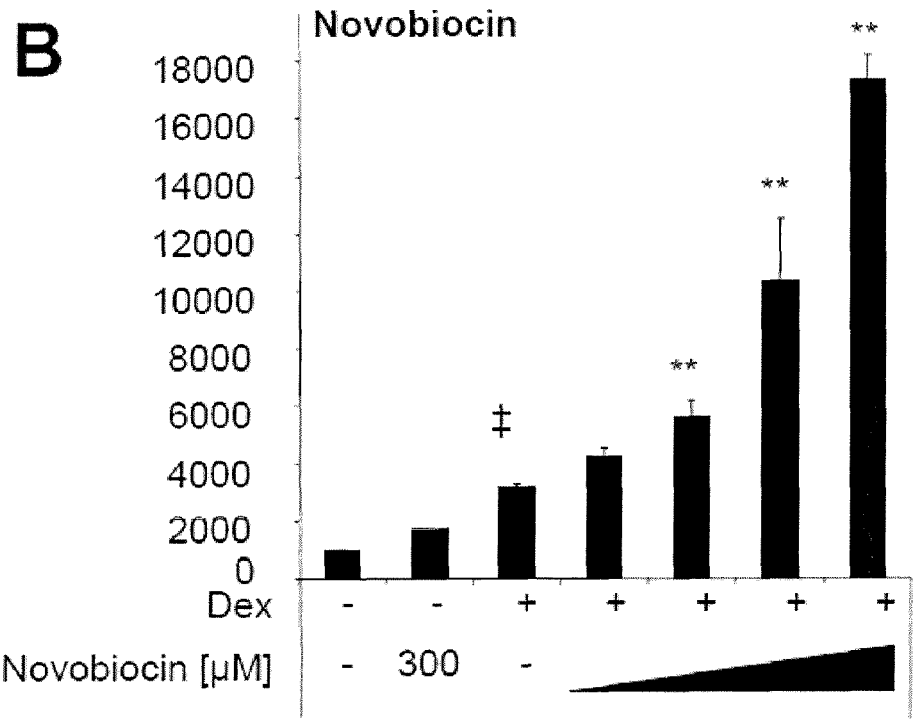
Figure 4C:
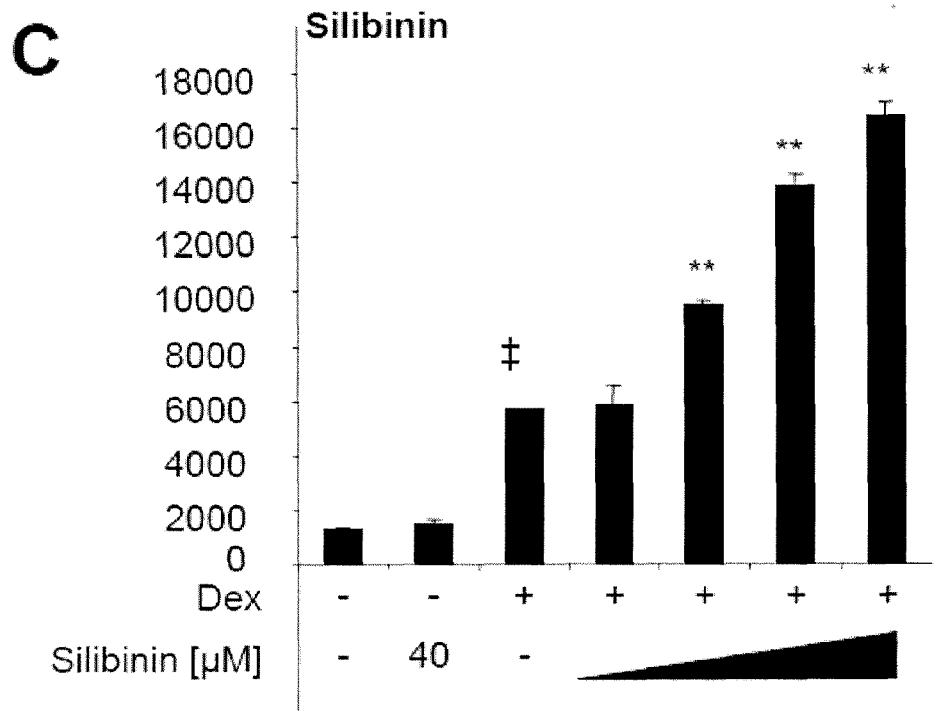
Figure 5:
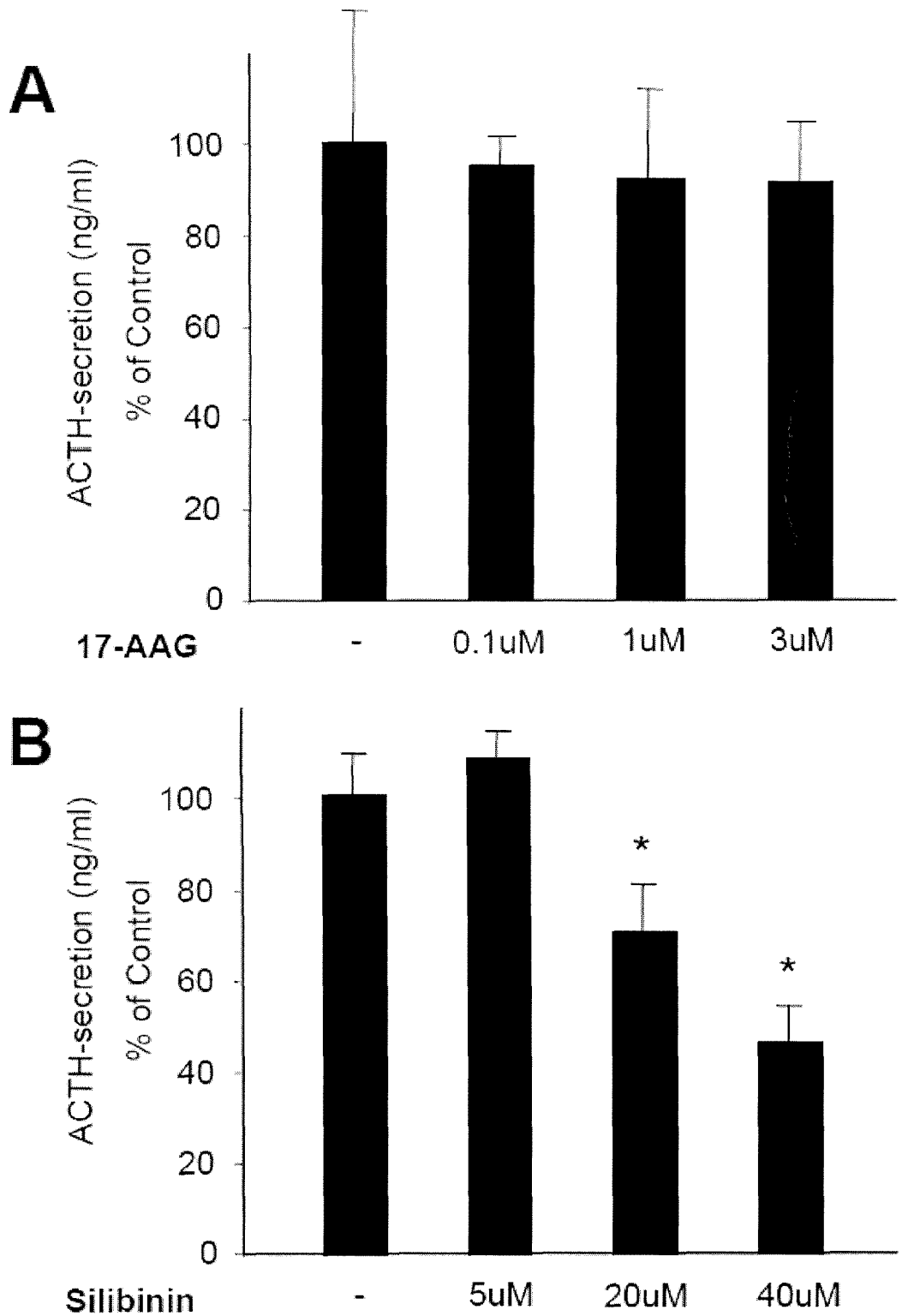
FIG. 5: C-terminal HSP90 inhibitors reduce ACTH secretion in corticotroph adenoma cells in the presence of glucocorticoids. AtT-20 cells were treated for 48 hours with the glucocorticoid dexamethasone (100 nM) plus different doses of 17-AAG or silibinin, as indicated in the figure. At the end of the treatment, ACTH was measured by RIA. A. 17-AAG has no effect on ACTH secretion. B. Silibinin inhibits ACTH secretion. *, $p<0.01$ as compared to control.
Figure 6:
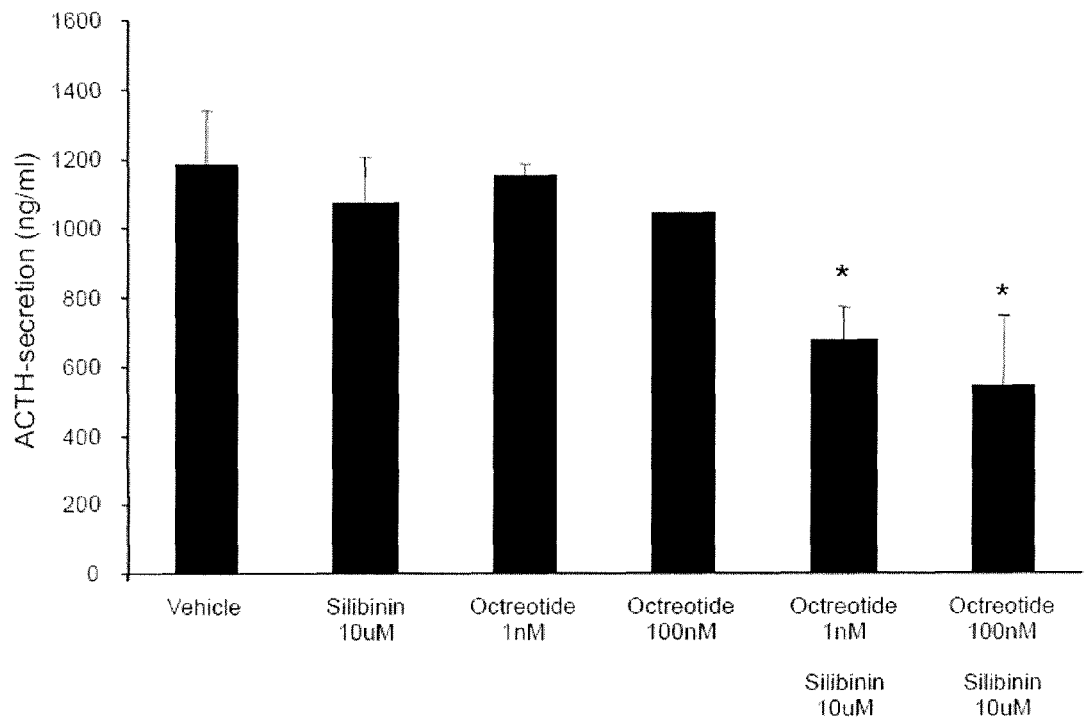
FIG. 6: Silibinin reduces ACTH production in corticotroph adenoma cells in combination with sub-optimal concentrations of the somatostatin analog octreotide. AtT-20 cells were treated for 72 hours with 10 μM silibinin in combination with different doses of octreotide, as indicated in the figure. At the end of the treatment, supernatants were collected, and ACTH was measured by RIA. *, $p<0.01$ as compared to the correspondent concentration of octreotide alone.

Abbreviations used in the present description have the following meanings:
17-AAG (17-N-Allylamino-17-demethoxygeldanamycin), 17-DMAG (17-Dimethylaminoethylamino-17-demethoxygeldanamycin), Asp (aspartic acid), Glu (glutamic acid), Met (methionine), Val (valine). ACTH (Adrenocorticotropic hormone), CCT018159 (4-[4-(2,3-Dihydro-1,4-benzodioxin-6-yl)-5-methyl-1H-pyrazol-3-yl]-6-ethyl-1,3-benzenediol), GR (glucocorticoid receptor).

EXAMPLES

Example 01

Immunohistochemistry

The immunohistochemical detection of HSP90 was performed with the streptavidin-biotin-peroxidase complex method on normal human pituitaries taken from autopsy samples of healthy subjects after accidental death and on tumor biopsies taken during trans-sphenoidal surgery from patients with Cushing's disease. The tissue samples were immediately frozen on dry ice and cut into histological sections. After hydration, primary antibodies directed against HSP90-alpha (Epitomics) were applied to the sections in a dilution 1:200. Then, the sections were washed and a secondary, anti-rabbit biotinylated antibody was applied. The antibodies were visualized with the ABC-complex and 3,3'-diaminobenzidine, producing a brown color. The slides were counterstained with toluidine-blue to visualize the cell nuclei.

Example 02

Proliferation Assay (WST-1 Assay)

Cell proliferation was measured with the WST-1 proliferation assay (Roche Applied Science). This assay measures the activity of the mitochondrial succinate dehydrogenase. After 4 days of treatment with different HSP90 inhibitors, the WST-1 reagent was added to AtT-20 cell cultures in 96-well plates to a final dilution of 1:10. The cells were incubated for 2 hours and then the absorbance of the reaction product was measured with an ELISA reader at 440 nm, following the manufacturer's instructions.

Example 03

Western Blot—Evaluation of the Induction of GR Degradation

AtT-20 cells in 6-well plates were treated with different HSP90 inhibitors for the times indicated in each experiment. At the end of the treatment, cell lysates were prepared in lysis buffer supplemented with protease and phosphatase inhibitor cocktail (Roche). Samples of the lysates were separated by PAGE and blotted onto membranes using standard western blot procedures with gels and buffers from Invitrogen. After blocking the membranes with 5% non-fat dry milk, primary antibodies against GR (H-300, Santa Cruz), Cdk1 (BD Transduction Laboratories), and actin (Cell Signalling) were added. Anti-mouse and anti-rabbit horseradish peroxidase-conjugated secondary antibodies were used to detect the primary antibodies. The detection was carried out using Lumilight (Roche) or ECL-Plus (Thermo Scientific).

Example 04

Evaluation of GR Activity

AtT-20 cells ($3\times10^5$) were transfected for 3 hours with 1 µg of the MTV-Luc reporter plasmid in 6-well plates. Cell transfection was performed with SuperFect (Qiagen GmbH). After an overnight incubation in culture medium with 10% fetal calf serum, the cells were treated with different HSP90 inhibitors in combination with dexamethasone. Luciferase activity in cell lysates was measured with a Berthold luminometer after addition of luciferin and ATP. Transfection efficiency was determined using the Rous sarcoma virus-β-gal construct. Data are expressed as the ratio of luciferase activity to β-gal activity.

Example 05

Evaluation of ACTH Secretion

AtT-20 cells were seeded in 96-well plates in cell culture medium containing dexamethasone to mimic the high glucocorticoid concentration in the blood of patients with Cushing's disease. The cultures were treated with different HSP90 inhibitors or octreotide, as indicated in the figures. At the end of the treatment, the cell culture supernatants were collected and frozen. ACTH secreted into the cell culture medium was measured by radio-immunoassay (RIA) in comparison with known amounts of ACTH standards diluted in the same medium. The RIA was performed using an N-terminal-specific anti-ACTH antibody and ACTH was labeled with $I^{125}$. The bound and free fractions were separated by centrifugation with charcoal and the radioactivity was measured in a beta-counter.

Example 06

Figure 10:
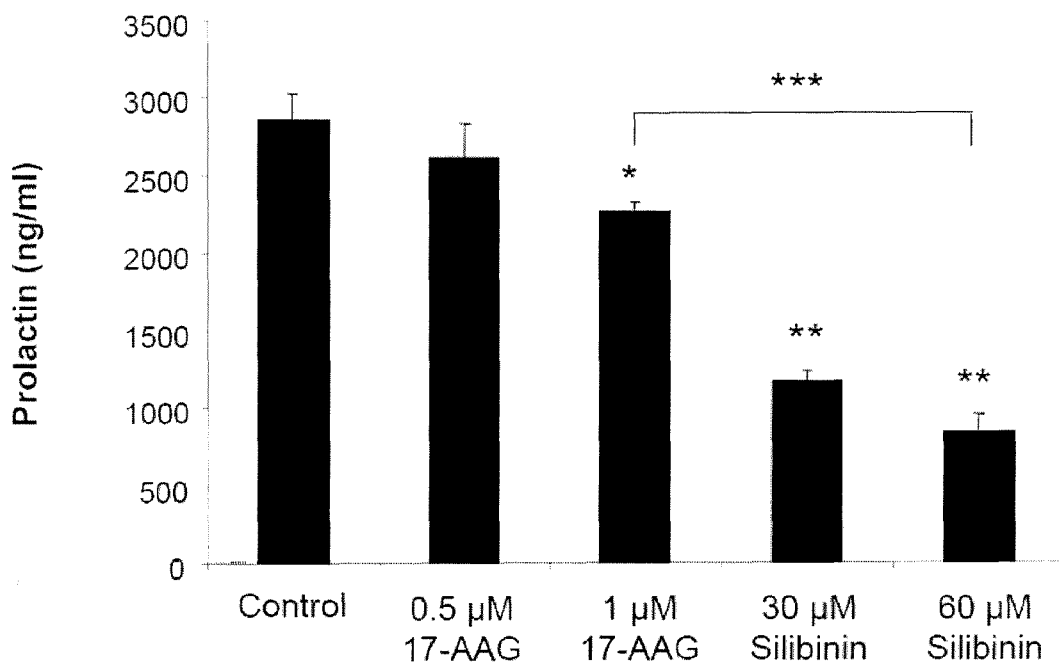
FIG. 10: C-terminal HSP90 inhibitors strongly reduce prolactin secretion in GH3 prolactinoma cells. 17-AAG minimally inhibited prolactin secretion only at a concentration of 1 μM. Higher concentrations of 17-AAG were toxic for GH3 cells, as measured by the cell-viability assay WST-1. Silibinin significantly inhibited the secretion of prolactin in the GH3 prolactinoma cell line. The inhibition was significantly stronger than the one produced by 17-AAG and no toxicity was observed, even at high concentrations. *, $p<0.01$; , $p<0.001$ as compared to control. *, $p<0.001$: comparison between the maximum inhibitions produced by 17-AAG and silibinin.

Evaluation of Prolactin Secretion 10,000 GH3 prolactinoma cells obtained from the American Type Culture Collection (Rockville, Md.) were seeded onto 96-well plates in DMEM with 10% fetal calf serum. After 24 hours the medium was changed and the attached cells were treated with different doses of the HSP90 inhibitors 17-AAG or silibinin, as indicated in FIG. 10. After 48 hours, culture supernatants were collected and the concentration of prolactin was measured by RIA. 17-AAG minimally inhibited prolactin secretion only at a concentration of 1 µM. Higher concentrations of 17-AAG were toxic for GH3 cells, as measured by the cell-viability assay WST-1. Silibinin significantly inhibited the secretion of prolactin in the GH3 prolactinoma cell line. The inhibition was significantly stronger than the one produced by 17-AAG and no toxicity was observed, even at high concentrations

Example 07

Figure 11:
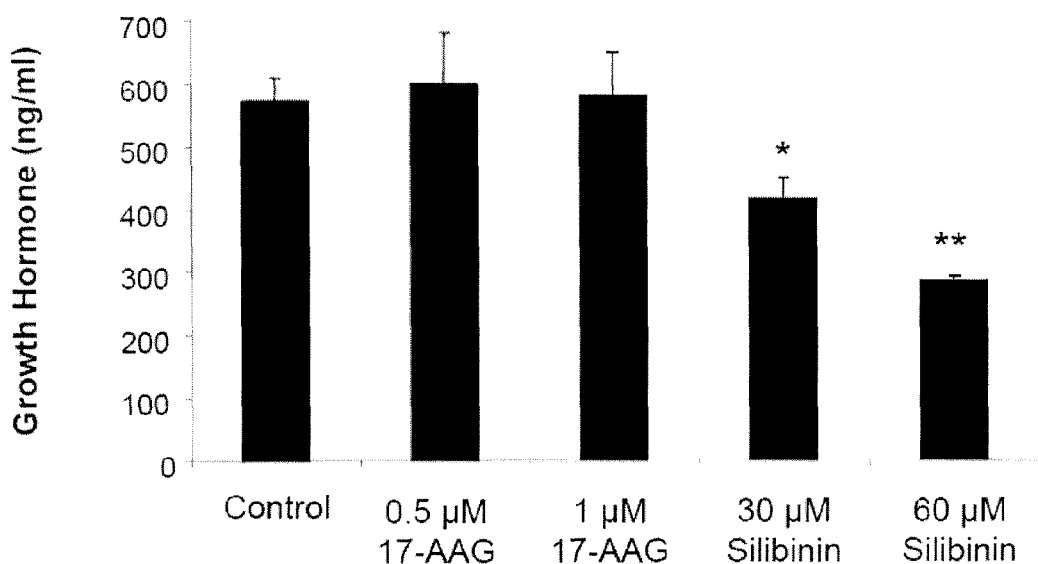
FIG. 11: C-terminal HSP90 inhibitors reduce growth hormone secretion in GH3 somatotroph adenoma cells. 17-AAG did not inhibit growth hormone secretion at any of the tested concentrations. Higher concentrations of 17-AAG were toxic for GH3 cells, as measured by the cell-viability assay WST-1. Silibinin significantly inhibited the secretion of growth hormone in the GH3 somatotroph adenoma cell line and no toxicity was observed, even at high concentrations. *, $p<0.01$; **, $p<0.001$.

Evaluation of Growth Hormone Secretion 10,000 GH3 somatotroph adenoma cells obtained from the American Type Culture Collection (Rockville, Md.) were seeded onto 96-well plates in DMEM with 10% fetal calf serum. After 24 hours the medium was changed and the attached cells were treated with different doses of the HSP90 inhibitors 17-AAG or silibinin, as indicated in the FIG. 11. After 48 hours, culture supernatants were collected and the concentration of growth hormone was measured by RIA. FIG. 11 shows that C-terminal HSP90 inhibitors reduce growth hormone secretion in GH3 somatotroph adenoma cells. 17-AAG did not inhibit growth hormone secretion at any of the tested concentrations. Higher concentrations of 17-AAG were toxic for GH3 cells, as measured by the cell-viability assay WST-1. Silibinin significantly inhibited the secretion of growth hormone in the GH3 somatotroph adenoma cell line and no toxicity was observed, even at high concentrations.

Example 08

Evaluation of the In Vivo Effects of *Silibum marianum* Extract 500,000 AtT-20 cells obtained from the American Type Culture Collection (Rockville, Md.) were suspended in PBS and injected subcutaneously in nude mice (nu/nu). After one week, the mice were randomized and started receiving daily an oral dose of either a *Silibum marianum* extract or vehicle alone. Each mouse in the treatment group received via oral gavage the amount of extract powder corresponding to 300 mg/Kg/day of silibinin dissolved in water. The source of the extract powder was Silicur from Hexal, Germany, containing 108.2 mg of silibinin per capsule. A control group of mice having corticotroph tumors received only vehicle. A second control group consisted in mice that did not have corticotroph tumors and did not receive any treatment. The tumor volume was measured twice weekly for 29 days. At the end of the treatment, the mice were sacrificed, blood samples were collected, and plasma was separated to measure ACTH and corticosterone using the respective RIA assays.

Figure 7:
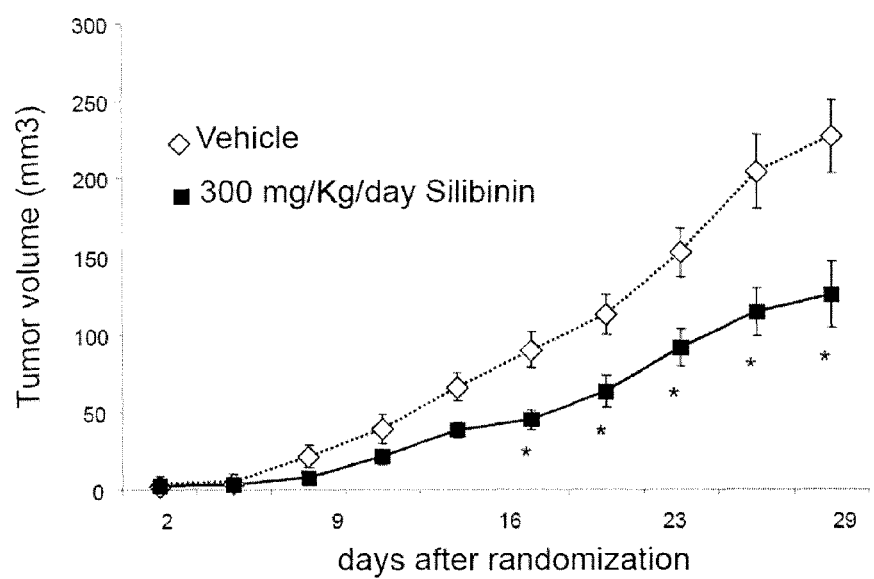
FIG. 7: *Silibum marianum* extract inhibits tumor growth in nude mice xenografts of AtT-20 corticotroph adenomas. The treatment with *Silibum marianum* extract containing silibinin significantly inhibited the growth of corticotroph adenomas as compared to vehicle. *, $p<0.01$.
Figure 8:
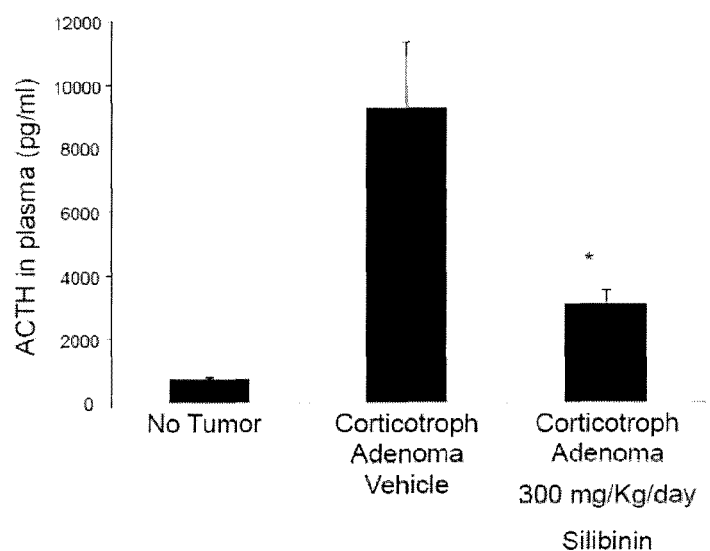
FIG. 8: *Silibum marianum* extract reduces ACTH plasma levels in a mouse model of Cushing's disease. The treatment with *Silibum marianum* extract containing silibinin significantly inhibited plasma ACTH in nude mice having xenografts of AtT-20 corticotroph adenomas as compared to vehicle-treated animals. "No tumor" represents the basal levels of ACTH. *, $p<0.01$.
Figure 9:
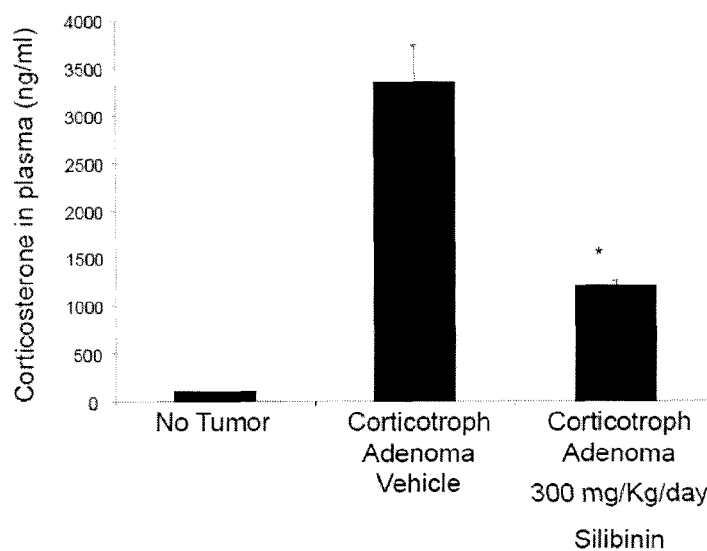
FIG. 9: *Silibum marianum* extract reduces the plasma levels of corticosterone in a mouse model of Cushing's disease. The treatment with *Silibum marianum* extract containing silibinin significantly inhibited plasma corticosterone in nude mice having xenografts of AtT-20 corticotroph adenomas as compared to vehicle-treated animals. "No tumor" represents the basal levels of corticosterone. *, $p<0.01$.

As shown in FIG. 7, after two weeks of treatment, *Silibum marianum* extract significantly inhibited the growth of corticotroph adenomas in mice. Additionally the treatment with *Silibum marianum* extract resulted in inhibition of the ACTH and corticosterone secretion (see FIG. 8 and FIG. 9).

The invention claimed is:

1. A method for treating a human suffering from a disease selected from the group consisting of corticotroph adenoma, lactotroph adenoma, somatotroph adenoma and thyrotroph adenoma, wherein said human is administered a therapeutically effective amount of a Silybum marianum extract to effectively treat the disease in said human, and wherein said Silybum marianum extract contains a compound of Formula (I):

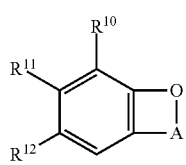

wherein

A is selected from

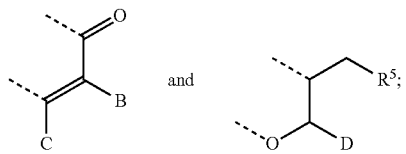

B represents —NH—C(O)—R$^{23}$, —NH—SO$_2$—R$^{23}$

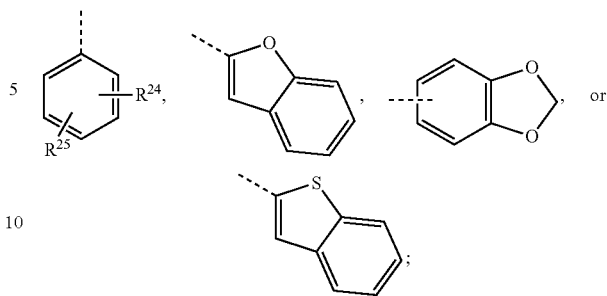

C represents —H or —OH;

D represents

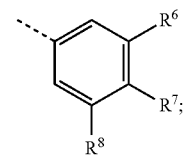

R$^{10}$ represents —H, —CH$_3$, —OCH$_3$, —F, —Cl, —Br, or —I;

R$^{11}$ represents —H, —OR$^{20}$, —OCH$_2$R$^{19}$, —CO$_2$H, —CH$_2$OH, —CO$_2$CH$_3$, —NH$_2$, —NH—C(O)—CH$_3$,

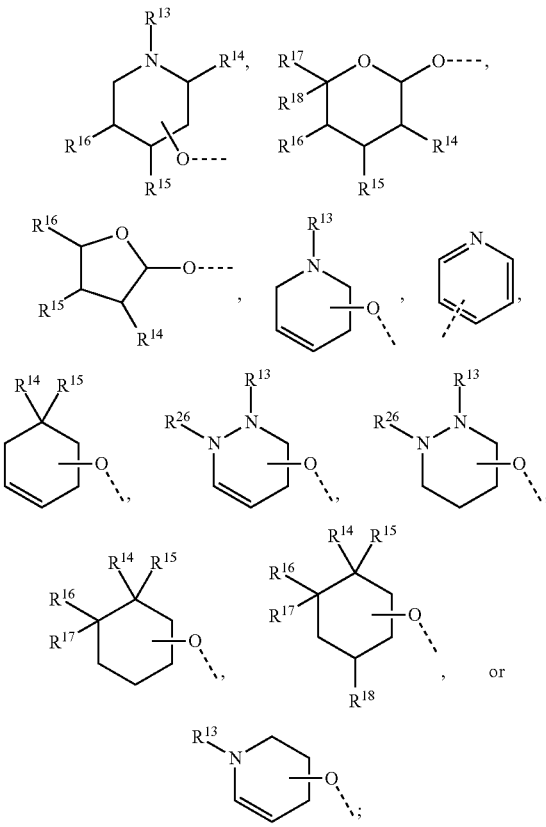

R$^{12}$ is selected from —H, —CH$_3$, —OCH$_3$, and

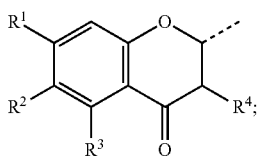

R[13] and R[26] are independently of each other —H, —CH$_3$, or —C(O)CH$_3$;

R[14], R[15], R[16], R[17] and R[18] are independently of each other selected from: —H, —OH, —NH$_2$, —OCH$_3$, —OC$_2$H$_5$, —CH$_3$, —O—C(O)—NH$_2$, —O—C(O)—NHR[22], —C$_2$H$_4$—S(O)$_2$(OCH$_3$), —C$_2$H$_4$—P(O)(OCH$_3$)$_2$, —CH$_2$—O—C(O)CH$_3$, —CH$_2$—NH—S(O)$_2$—OCH$_3$,

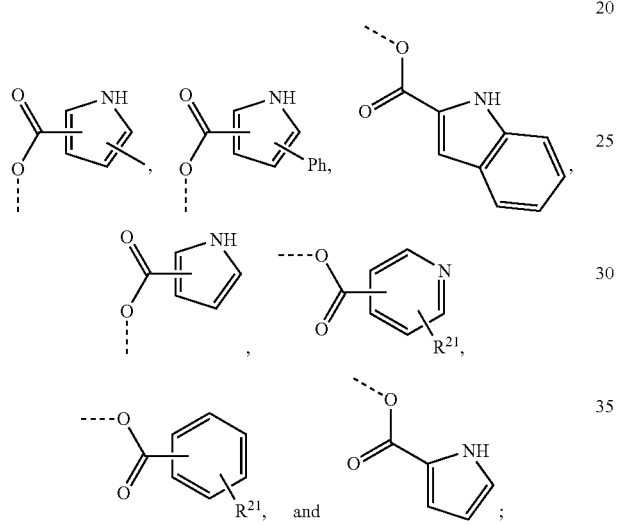

R[19] represents —CH$_2$—NH$_2$, —CH$_2$—NHCH$_3$, —CH(OH)—CH$_2$(OH),

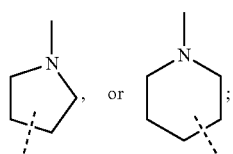

R[20] represents —H, —C(O)—CH$_3$, —C(O)—C$_2$H$_5$, —C(O)—C$_3$H$_7$, —C(O)—NH$_2$, —C(O)—NH—CH$_3$, —C(O)—NH—C$_2$H$_5$, —SO$_2$(CH$_3$),

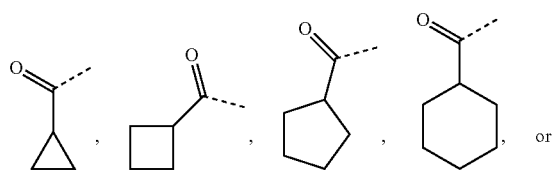

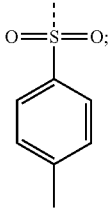

R[21] represents —H, —OH, —SH, —CH$_3$, —C$_2$H$_5$, —F, —Cl, —Br, or —I;

R[22] represents —CH$_3$, —C$_2$H$_5$, —C$_3$H$_7$, —C$_4$H$_9$,

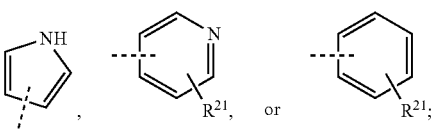

R[23] represents —CH$_3$, —C$_2$H$_5$, —C$_3$H$_7$, —C$_4$H$_9$, —CH$_2$-Ph, —C$_2$H$_4$-Ph, —O—CH$_2$-Ph,

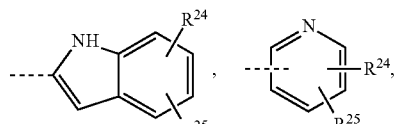

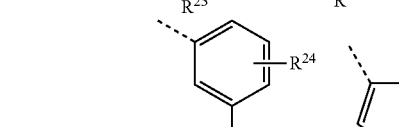

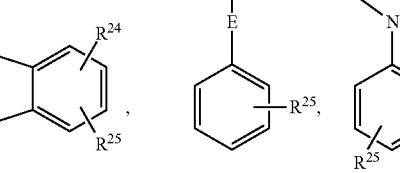

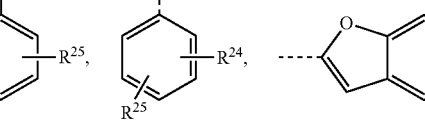

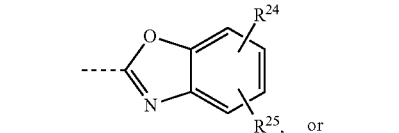

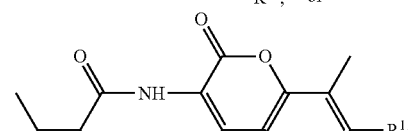

R[24] and R[25] are independently of each other selected from —H, —OH, —OCH$_3$, —OC$_2$H$_5$, —OPh, —O—CH$_2$-

Ph, —CH₂-Ph, —C₂H₄-Ph, —NH₂, —NO₂, —CH₂—CH=C(CH₃)₂, —CH=CHPh, —F, —Cl, —Br, —I, —CN, —CH₃, —C₂H₅, —C₃H₇, —C₄H₉, —OCF₃, —CF₃, —C(CH₃)₃, and -Ph; or $R^{24}$ together with $R^{25}$ form together with the 2 aromatic carbons they are connected to a cycle selected from:

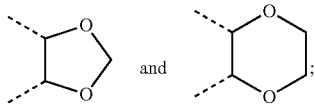

E represents —O—, —S—, —NH—, —CH₂—, or —OCH₂—;

$R^1$, $R^2$, $R^3$, $R^4$, $R^6$, $R^7$ and $R^8$ represent independently of each other —H, —OH, —OCH₃, or —OC₂H₅;

$R^5$ represents —H or —OR⁹;

$R^9$ represents —H, —CH₃, —C₂H₅, -βGlc, -βGal, -βMal, or -βLac; and enantiomers, stereoisomeric forms, mixtures of enantiomers, diastereomers, mixtures of diastereomers, hydrates, solvates, acid salt forms, tautomers, or racemates of the above mentioned compounds or pharmaceutically acceptable salts thereof.

2. The method according to claim 1, wherein the compound has the following general formula (II)

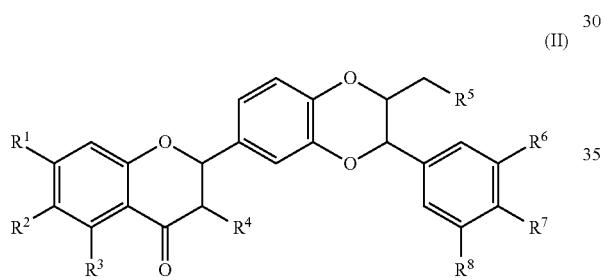

(II)

wherein $R^1$, $R^2$, $R^3$, $R^4$, $R^6$, $R^7$ and $R^8$ represent independently of each other —H, —OH, —OCH₃, or —OC₂H₅;

$R^5$ represents —H or —OR⁹; and $R^9$ represents —H, —CH₃, —C₂H₅, -βGlc, -βGal, -βMal, or -βLac; and enantiomers, stereoisomeric forms, mixtures of enantiomers, diastereomers, mixtures of diastereomers, anomers, hydrates, solvates, acid salt forms, tautomers, or racemates of the above mentioned compounds, or pharmaceutically acceptable salts thereof.

3. The method according to claim 2, wherein the compound has the following general formula (III)

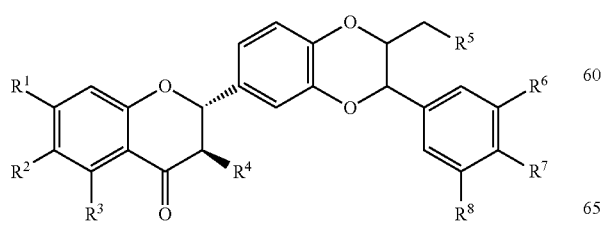

(III)

wherein $R^1$, $R^3$, $R^4$ and $R^7$ represent —OH;

$R^2$ and $R^8$ represent —H;

$R^5$ represents —OR⁹;

$R^6$ represents —OCH₃; and $R^9$ represents —H, —CH₃, —C₂H₅, -βGlc, -βGal, -βMal, or -βLac; and diastereomers, mixtures of diastereomers, anomers, hydrates, solvates, acid salt forms of the above mentioned compounds, or pharmaceutically acceptable salts thereof.

4. The method according to claim 1, wherein the compound has general formula (I),

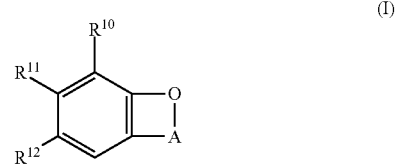

(I)

wherein

A represents

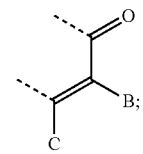

B represents —NH—C(O)—R²³, —NH—SO₂—R²³,

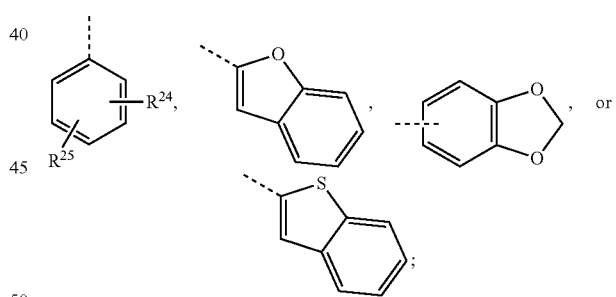

C represents —H or —OH;

$R^{10}$ represents —H, —CH₃, —OCH₃, —F, —Cl, —Br, or —I;

$R^{11}$ represents —OR²⁰, —OCH₂R¹⁹, —CO₂H, —CH₂OH, —CO₂CH₃, —NH₂, —NH—C(O)—CH₃,

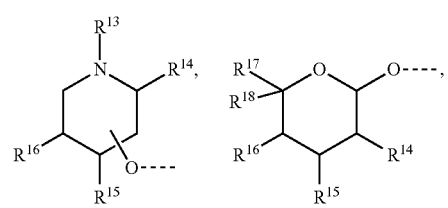

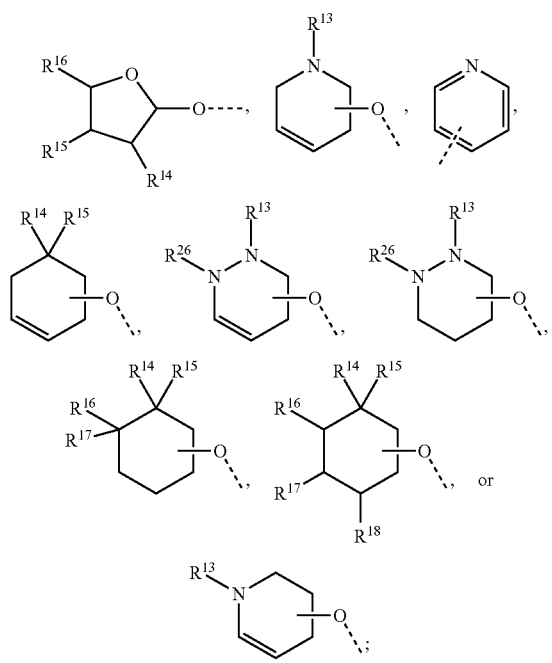

$R^{12}$ represents —H, —CH$_3$, or —OCH$_3$;

$R^{13}$ and $R^{26}$ are independently of each other —H, —CH$_3$, or —C(O)CH$_3$;

$R^{14}$ $R^{15}$ $R^{16}$ $R^{17}$ and $R^{18}$ are independently of each other selected from: —H, —OH, —NH$_2$, —OCH$_3$, —OC$_2$H$_5$, —CH$_3$, —O—C(O)—NH$_2$, —O—C(O)—NHR$^{22}$, —C$_2$H$_4$—S(O)$_2$—OCH$_3$, —C$_2$H$_4$—P(O)(OCH$_3$)$_2$, —CH$_2$—O—C(O)CH$_3$, —CH$_2$—NH—S(O)$_2$—OCH$_3$,

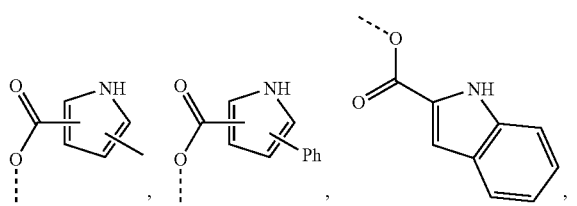

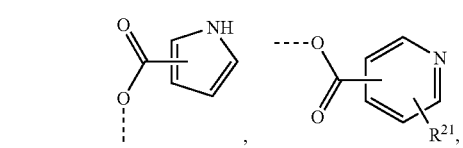

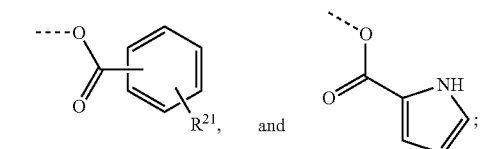

$R^{19}$ represents —CH$_2$—NH$_2$, —CH$_2$—NHCH$_3$, —CH(OH)—CH$_2$(OH),

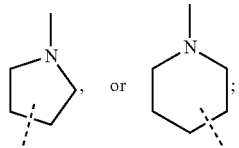

$R^{20}$ represents —H, —C(O)—CH$_3$, —C(O)—C$_2$H$_5$, —C(O)—C$_3$H$_7$, —C(O)—NH$_2$, —C(O)—NH—CH$_3$, —C(O)—NH—C$_2$H$_5$, —SO$_2$(CH$_3$),

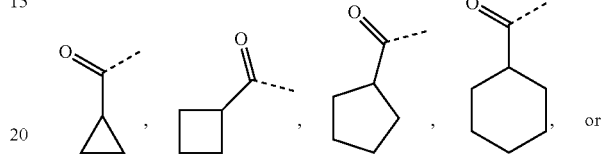

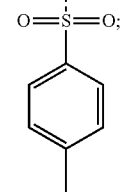

$R^{21}$ represents —H, —OH, —SH, —CH$_3$, —C$_2$H$_5$, —F, —Cl, —Br, or —I;

$R^{22}$ represents —CH$_3$, —C$_2$H$_5$, —C$_3$H$_7$, or —C$_4$H$_9$,

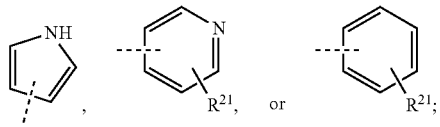

$R^{23}$ represents —CH$_3$, —C$_2$H$_5$, —C$_3$H$_7$, —C$_4$H$_9$, —CH$_2$-Ph, —C$_2$H$_4$-Ph, —O—CH$_2$-Ph,

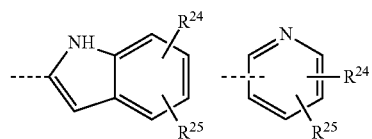

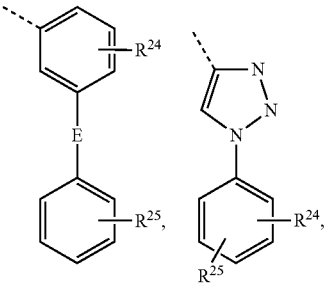

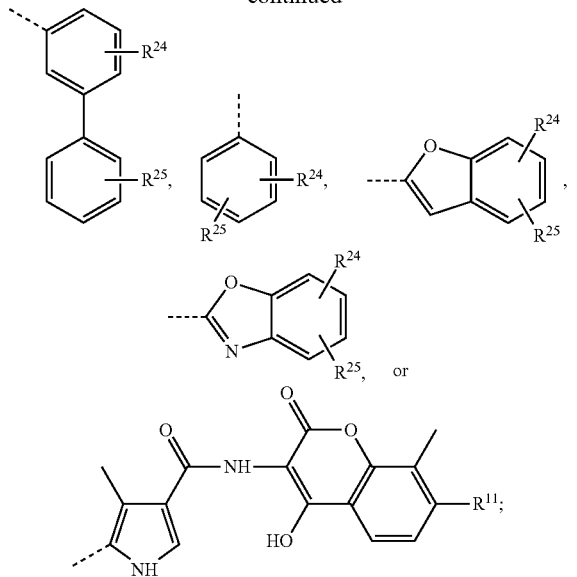

$R^{24}$ and $R^{25}$ are independently of each other selected from —H, —OH, —OCH$_3$, —OC$_2$H$_5$, —OPh, —O—CH$_2$-Ph, —CH$_2$-Ph, —C$_2$H$_4$-Ph, —NH$_2$, —NO$_2$, —CH$_2$—CH=C(CH$_3$)$_2$, —CH=CHPh, —F, —Cl, —Br, —I, CN, —CH$_3$, —C$_2$H$_5$, —C$_3$H$_7$, —C$_4$H$_9$, —OCF$_3$, —CF$_3$, —C(CH$_3$)$_3$, and -Ph;

$R^{24}$ together with $R^{25}$ form together with the 2 aromatic carbons they are connected to a cycle selected from:

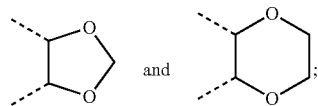

E represents —O—, —S—, —NH—, —CH$_2$—, or —OCH$_2$—; and enantiomers, stereoisomeric forms, mixtures of enantiomers, diastereomers, mixtures of diastereomers, anomers, hydrates, solvates, acid salt forms, tautomers, or racemates of the above mentioned compounds, or pharmaceutically acceptable salts thereof.

* * * * *